US012612430B2

(12) United States Patent
Janson et al.

(10) Patent No.: US 12,612,430 B2
(45) Date of Patent: Apr. 28, 2026

(54) PEPTIDES

(71) Applicant: ENLITISA (SHANGHAI) PHARMACEUTICAL CO., LTD., Shanghai (CN)

(72) Inventors: Jan-Christer Janson, Uppsala (SE); Ming Gu, Jiangyin (CN); Bengt Ingemar Samuelsson, Solna (SE); Maoqian Song, Jiangyin (CN)

(73) Assignee: ENLITISA (SHANGHAI) PHARMACEUTICAL CO., LTD., Shanghai (CN)

( * ) Notice: Subject to any disclaimer, the term of this patent is extended or adjusted under 35 U.S.C. 154(b) by 595 days.

(21) Appl. No.: 17/642,764

(22) PCT Filed: Sep. 11, 2020

(86) PCT No.: PCT/CN2020/114828
§ 371 (c)(1),
(2) Date: Mar. 14, 2022

(87) PCT Pub. No.: WO2021/047648
PCT Pub. Date: Mar. 18, 2021

(65) Prior Publication Data
US 2024/0124521 A1 Apr. 18, 2024

(30) Foreign Application Priority Data
Sep. 14, 2019 (WO) ............... PCT/CN2019/105830

(51) Int. Cl.
| | |
|---|---|
| *C07K 7/06* | (2006.01) |
| *A61K 8/64* | (2006.01) |
| *A61P 29/00* | (2006.01) |
| *A61Q 19/00* | (2006.01) |
| *A61K 38/00* | (2006.01) |

(52) U.S. Cl.
CPC ................. *C07K 7/06* (2013.01); *A61K 8/64* (2013.01); *A61P 29/00* (2018.01); *A61Q 19/00* (2013.01); *A61K 38/00* (2013.01)

(58) Field of Classification Search
CPC ............. C07K 7/06; A61P 29/00; A61K 8/64
See application file for complete search history.

(56) References Cited

U.S. PATENT DOCUMENTS

| | | | |
|---|---|---|---|
| 4,585,585 A | 4/1986 | Waite | |
| 4,908,404 A | 3/1990 | Benedict et al. | |
| 5,015,677 A | 5/1991 | Benedict et al. | |
| 5,024,933 A | 6/1991 | Yang et al. | |
| 5,616,311 A * | 4/1997 | Yen ...................... | A61K 9/5169 |
| | | | 977/797 |
| 2017/0190746 A1* | 7/2017 | Cha ..................... | A61L 24/0015 |
| 2018/0221444 A1* | 8/2018 | Janson ..................... | A61K 8/64 |
| 2018/0228873 A1* | 8/2018 | Samuelsson ............ | A61P 17/04 |
| 2024/0218016 A1 | 7/2024 | Gu et al. | |

FOREIGN PATENT DOCUMENTS

| | | | | |
|---|---|---|---|---|
| BR | 112018013246 A2 * | 12/2018 | ............. | C07K 14/00 |
| CN | 110312513 A | 10/2019 | | |
| CN | 112236440 A | 1/2021 | | |
| KR | 101677097 B1 | 11/2016 | | |
| WO | 88/07076 A1 | 9/1988 | | |
| WO | 96/39128 A1 | 12/1996 | | |
| WO | WO 96/39128 * | 12/1996 | ............... | A61K 9/64 |
| WO | 00/15789 A1 | 3/2000 | | |
| WO | 03/008376 A2 | 1/2003 | | |

(Continued)

OTHER PUBLICATIONS

Waite, 1987, Nature's underwater adhesive specialist, Int J Adhesion and Adhesives, 7(1): 9-14.*
Burzio et al., 2000, Cross-Linking in Adhesive Quinoproteins: Studies with Model Decapeptides, Biochemistry, 39: 11147-11153.*
Fang et al., 2007, Functional Group Approaches to Prodrugs: Functional Groups in Peptides, Chapter 3.7, pp. 965-988, Prodrugs: Challenges and Rewards Part 1, Eds Stella, Borchardt, Hageman, Oliyai, Maag, and Tilley.*
Borchardt et al., 1999, Optimizing oral absorption of peptides using prodrug strategies, Journal of Controlled Release, 62: 231-238.*
Waite J.H., "Nature's Underwater Adhesive Specialist," Int. J. Adhesion and Adhesives 7(1):9-14 (1987).

(Continued)

*Primary Examiner* — Amber D Steele

(74) *Attorney, Agent, or Firm* — Troutman Pepper Locke LLP (Rochester)

(57) ABSTRACT

Provided is a peptide compound comprising the amino acid sequence: $Xaa_1$-Lys-$Xaa_3$-Ser-$Xaa_5$-$Xaa_6$-$Xaa_7$-$Xaa_8$-$Xaa_9$-$Xaa_{10}$-$Xaa_{11}$-$Xaa_{12}$-$Xaa_{13}$ wherein: $Xaa_1$ represents Ala or Ser, or is absent, wherein the N-terminal amino acid optionally includes an N-terminal 3,4-dihydrocinnamic acid group; $Xaa_5$ represents Tyr, DOPA or a single bond; $Xaa_3$ and $Xaa_6$ independently represent Pro, Hyp or diHyp; $Xaa_7$, $Xaa_8$, $Xaa_9$, $Xaa_{10}$, and $Xaa_{11}$ are each optional (in which case $Xaa_6$ is bonded to $Xaa_{12}$), and are independently selected from the group Pro, Hyp, diHyp, Thr, DOPA and Tyr; $Xaa_{12}$ represents Pro, Hyp, diHyp, Thr, DOPA or Tyr; and $Xaa_{13}$ represents Lys or is absent, as well as regioisomers, stereoisomers, and pharmaceutically- or cosmetically-acceptable salts of said peptide compound, provided that when the N-terminal 3,4-dihydrocinnamic acid group is not present, $Xaa_1$ represents Ala or is absent and $Xaa_{13}$ represents Lys, then $Xaa_{12}$ represents Pro, Hyp, diHyp or Thr. The compounds are particularly useful in for treatment of conditions characterised by inflammation, including wounds, burns, and disorders of the mucosa, such as anorectal diseases, inflammatory bowel diseases, gynaecological diseases and dental diseases.

22 Claims, 1 Drawing Sheet
Specification includes a Sequence Listing.

(56) References Cited

FOREIGN PATENT DOCUMENTS

| WO | 2007/124593 A1 | 11/2007 |
| WO | 2009/001220 A2 | 12/2008 |
| WO | 2017/011982 A1 | 1/2017 |
| WO | 2017/028777 A1 | 2/2017 |
| WO | 2017/088177 A1 | 6/2017 |
| WO | 2019/007356 A1 | 1/2019 |
| WO | 2019007355 A1 | 1/2019 |
| WO | 2019/059504 A1 | 3/2019 |
| WO | 2019/228307 A1 | 12/2019 |
| WO | 2020/052677 A1 | 3/2020 |

OTHER PUBLICATIONS

Burzio et al., "Cross-Linking in Adhesive Quinoproteins: Studies with Model Decapeptides," Biochemistry 39(36):11147-11153 (2000).

Quan et al., "Mussel-Inspired Catechol-Functionalized Hydrogels and Their Medical Applications," Molecules 24:1-27 (2019).

Zhu et al., "Composition, Working Mechanism and Application of Mussel Adhesive Protein," Advances in Marine Science 32(4):560-568 (2014).

Gao et al., "Review on Mussel Adhesive Protein," J. Anhui Agr. Sci. 39(32):19860-19862 (2011).

Yamamoto J., "Synthesis and Adhesive Studies of Marine Polypeptides," Chem. Soc., Perkin Trans. i:613-618 (1987).

Dalsin et al., "Mussel Adhesive Protein Mimetic Polymers for the Preparation of Nonfouling Surfaces," J. Am. Chem. Soc. 125:4253-4258 (2003).

Xiao et al., "Rebounding Triad (Severe Itching, Dryness and Burning) After Facial Corticosteroid Discontinuation Defines a Specific Class of Corticosteroid-dependent Dermatitis," J. Dermatol. 42(2):697-702 (2015).

Lu et al., "Facial Corticosteroid Addictive Dermatitis in Guiyang City, China," Clin. Exp. Dermatol. 35(6):618-621 (2010).

International Search Report and Written Opinion for corresponding Application No. PCT/CN2020/133436, (mailed Feb. 25, 2021).

Kanyalkar et al., "Conformation of a Model Peptide of the Tandem Repeat Decapeptide in Mussel Adhesive Protein by NMR and MD Simulations," Biomaterials. 23:389-396 (2002).

Waite, J.H., "Evidence for a Repeating 3, 4-Dihydroxyphenylalanine- and Hydroxyproline-containing Decapeptide in the Adhesive Protein of the Mussel, Mytilus edulis L," the Journal of Biological Chemistry 258:2911-2915 (1983).

International Search Report and Written Opinion for corresponding Application No. PCT/CN2019/105830 (mailed Jun. 15, 2020 ).

Waite, J., "Marine Adhesive Proteins: Natural Composite Thermosets," Int. J. Bio. Macromol. 12(2):139-144 (1990).

Sever and Wilker, "Synthesis of Peptides Containing DOPA (3, 4-dihydroxyphenylalanine)," Tetrahedron 57:6139-6146 (2001).

Fichman et al., "The Use of the Calcitonin Minimal Recognition Module for the Design of DOPA-Containing Fibrillar Assemblies," Nanomaterials 4:726-740 (2014).

Silverman et al., "Understanding Marine Mussel Adhesion," Marine Biotechnology 9(6):661-681. 2007.

International Search Report and Written Opinion for corresponding Application No. PCT/CN2020/114828 (mailed Dec. 14, 2020).

Waite, J., "Marine Adhesive Proteins: Natural Composite Thermosets," Int. J. Bio. Macromol. 12(2):139-144 (1990) [Abstract] Abstract only.

Taylor et al., "Polarographic and Spectrophotometric Investigation of Iron (III) Complexation to 3,4-Dihydroxyphenylalanine-Containing Peptides and Proteins from Mytilus edulis," Inorganic Chemistry 33(25):5819-5824 (1994).

Hwang et al., "Promotion of osteoblast proliferation on complex coacervation-based hyaluronic acid—recombinant mussel adhesive protein coatings on titanium," Biomaterials, Elsevier, Amsterdam, NL 31(6):1080-1084 (2010).

Nakashima et al., "Enzyme Control Over Coacervation," Methods in Enzymology 646:353-389 (2021).

Fang et al., "Functional Group Approaches to Prodrugs: Functional Groups in Peptides," Chapter 3.7, pp. 265-288, in Biotechnology: Pharmaceutical Aspects (2007).

* cited by examiner

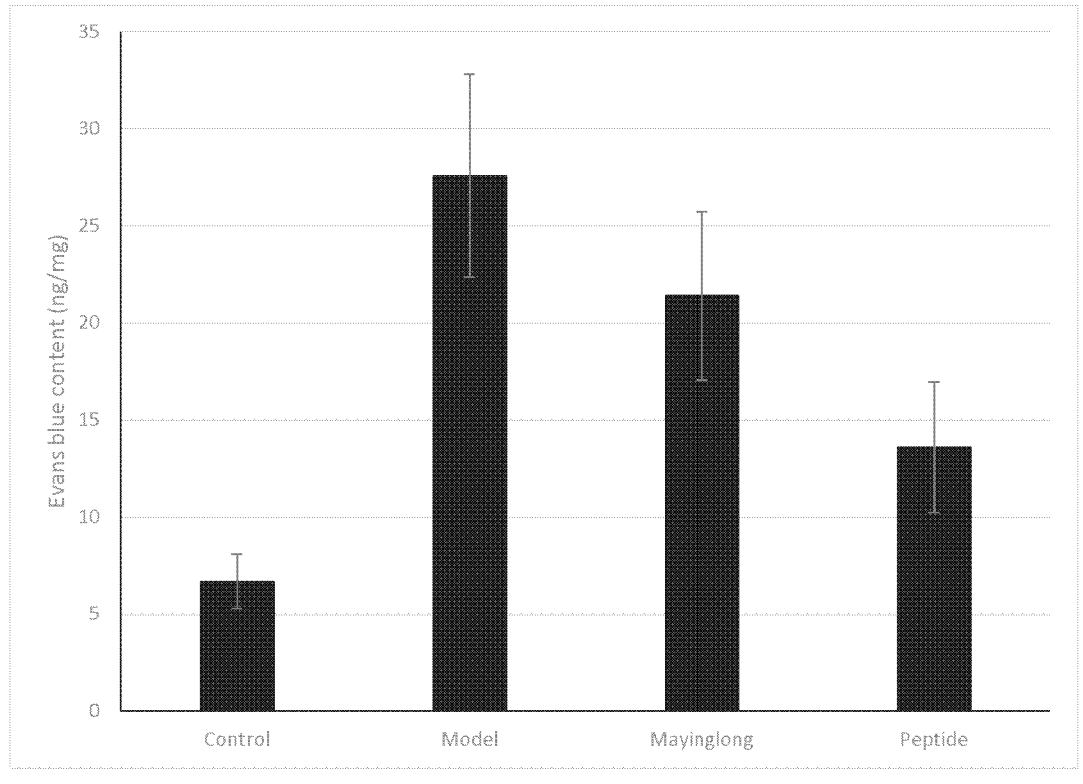

PEPTIDES

This application is a national stage application under 35 U.S.C. § 371 of International Application No. PCT/CN2020/114828, filed Sep. 11, 2020, which claims the priority benefit of International Application No. PCT/CN2019/105830, filed Sep. 14, 2019.

FIELD OF THE INVENTION

This invention relates to new, short-chain oligopeptides, the use of such peptides in human medicine, and to pharmaceutical compositions comprising them. In particular, the invention relates to the use of those peptides and compositions in the treatment of e.g. inflammation.

BACKGROUND AND PRIOR ART

Inflammation is typically characterized as a localised tissue response to e.g. invasion of microorganisms, certain antigens, damaged cells or physical and/or chemical factors. The inflammatory response is normally a protective mechanism which serves to destroy, dilute or sequester both the injurious agent and the injured tissue, as well as to initiate tissue healing.

Inflammation may result from physical trauma, infection, some chronic diseases (e.g. psoriasis and autoimmune diseases, such as rheumatoid arthritis) and/or chemical and/or physiological reactions to external stimuli (e.g. as part of an allergic response). A complex series of events may be involved, in which inflammatory mediators increase blood flow and dilation of local blood vessels, resulting in redness and heat, the exudation of fluids, often resulting in localised swelling, leukocytic migration into the inflamed area, and pain.

Many conditions/disorders are characterized by, and/or are caused by, abnormal, tissue-damaging inflammation. Such conditions are typically characterized by activation of immune defence mechanisms, resulting in an effect that is more harmful than beneficial to the host, and are generally associated with varying degrees of tissue redness or hyperemia, swelling, hyperthermia, pain, itching, cell death, tissue destruction, cell proliferation and/or loss of function. Examples include inflammatory bowel diseases, rheumatoid arthritis, multiple sclerosis, psoriasis, glomerulonephritis and transplant rejection.

Typically, a complex series of events results in inflammatory changes such as increased blood flow through dilation of local blood vessels, resulting in redness and heat, the extravasation of leukocytes and plasma, often resulting in localised swelling, activation of sensory nerves (resulting in pain in some tissues) and loss of function. These inflammatory changes are triggered by a cascade of cellular and biochemical events involving cells like neutrophils, monocytes, macrophages and lymphocytes together with inflammatory mediators such as vasoactive amines, cytokines, complement factors and reactive oxygen species.

Amongst other things, inflammation plays a key role in the wound healing process. Wounds and burns can therefore be classified as conditions with which inflammation is associated. Traditional thinking in the art is that anti-inflammatory drugs should not be applied directly to open wounds, as this would be detrimental to the progress of wound healing.

Fibrosis is defined by the excessive accumulation of fibrous connective tissue (components of the extracellular matrix (ECM) such as collagen and fibronectin) in and around inflamed or damaged tissue. Although collagen deposition is typically a reversible part of wound healing, it can often evolve into a progressively irreversible fibrotic response if tissue injury is severe, or if the wound-healing response itself becomes dysregulated. Furthermore, fibrogenesis is known to be a major cause of morbidity and mortality in many chronic inflammatory diseases, as well as end-stage liver disease, kidney disease, idiopathic pulmonary fibrosis (IPF) and heart failure. It is also a pathological feature of many chronic autoimmune diseases, such as scleroderma, rheumatoid arthritis, Crohn's disease, ulcerative colitis, myelofibrosis and systemic lupus erythematosus. Fibrosis may also influence the pathogenesis of many progressive myopathies, metastasis and graft rejection.

Mussel adhesive protein (MAP), also known as *Mytilus edulis* foot protein (mefp), is a protein that is secreted by marine shellfish species, such as *Mytilus edulis, Mytilus coruscus* and *Perna viridis*. Eleven identified separate adhesive protein subtypes have been derived from mussels, including the collagens pre-COL-P, pre-COL-D and pre-COL-NG; the mussel feet matrix proteins PTMP (proximal thread matrix protein) and DTMP (distal thread matrix protein); and mfp proteins mfp-2 (sometimes referred to as "mefp-2", hereinafter used interchangeably), mfp-3/mefp-3, mfp-4/mefp-4, mfp-5/mefp-5, mfp-6/mefp-6 and, most preferably mfp-1/mefp-1 (see, for example, Zhu et al, *Advances in Marine Science*, 32, 560 (2014) and Gao et al, *Journal of Anhui Agr. Sci.*, 39, 19860 (2011)).

A significant portion of mefp-1 consists of 70 to 90 tandem repeats of the decapeptide: Ala-Lys-Pro-Ser-Tyr-Xaa-Xaa-Thr-Xaa-Lys (SEQ ID No: 1; see Waite, Int. *J. Adhesion and Adhesives*, 7, 9 (1987)). This decapeptide sequence may be isolated as a low molecular weight derivative of naturally-occurring MAPS, or may be synthesized, for example as described by Yamamoto in *J. Chem. Soc., Perkin Trans.* 1, 613 (1987). See also Dalsin et al, *J. Am. Chem. Soc.*, 125, 4253 (2003). Xaa at positions 6 and 7 represents hydroxyproline (Hyp) residues; and Xaa at position 9 represents 3,4-dihydroxyphenylalanine (DOPA).

Analogues of the decapeptide, notably Ala-Lys-Pro-Ser-Tyr-Xaa-Xaa-Thr-Tyr-Lys (SEQ ID No: 2) have also been disclosed, where Xaa at positions 6 and 7 represents hydroxyproline (Hyp). See, for example, U.S. Pat. No. 5,616,311 and WO 96/39128.

There is a clear need for new and/or improved medicines that may be used in the treatment of inflammation and conditions characterised thereby.

DISCLOSURE OF THE INVENTION

According to a first aspect of the invention, there is provided an (isolated) peptide compound of the amino acid sequence:

(SEQ ID No: 3)
$Xaa_1$-Lys-$Xaa_3$-Ser-$Xaa_5$-$Xaa_6$-$Xaa_7$-$Xaa_8$-$Xaa_9$-$Xaa_{10}$-

$Xaa_{11}$-$Xaa_{12}$-$Xaa_{13}$ wherein:

$Xaa_1$ represents Ala or Ser, or is absent (in which case, Lys is the N-terminal amino acid), wherein the N-terminal amino acid optionally includes an N-terminal 3,4-dihydrocinnamic acid group;

$Xaa_5$ represents Tyr, DOPA or a single bond (i.e. is absent);

$Xaa_3$ and $Xaa_6$ independently represent Pro, Hyp or diHyp;

$Xaa_7$, $Xaa_8$, $Xaa_9$, $Xaa_{10}$, and $Xaa_{11}$ are each optional (in which case $Xaa_6$ is bonded to $Xaa_{12}$), and are independently selected from the group Pro, Hyp, diHyp, Thr, DOPA and Tyr;

$Xaa_{12}$ represents Pro, Hyp, diHyp, Thr, DOPA or Tyr; and $Xaa_{13}$ represents Lys or is absent (in which case $Xaa_{12}$ represents the C-terminal amino acid), as well as regioisomers, stereoisomers, and pharmaceutically- or cosmetically-acceptable salts of said peptide compound, provided that when the N-terminal a 3,4-dihydrocinnamic acid group is not present, $Xaa_1$ represents Ala or is absent and $Xaa_{13}$ represents Lys, then $Xaa_{12}$ represents Pro, Hyp, diHyp or Thr (i.e. $Xaa_{12}$ does not represent DOPA or Tyr), which compounds, regioisomers, stereoisomers and salts are referred to together hereinafter as 'the compounds of the invention'. Hyp as recited with respect to SEQ ID NOS: 3-41 recited herein independently represents 3-hydroxyproline, 4-hydroxyproline, or 5-hydroxyproline. DiHyp as recited with respect to SEQ ID NOS: 3-41 represents 4,5-dihydroxyproline. DOPA as recited herein with respect to SEQ ID NOS: 3-41 recited herein represents 3,4-dihydroxyphenylalanine.

Compounds of the invention that may be mentioned include those in which: the N-terminal a 3,4-dihydrocinnamic acid group of $Xaa_1$ is not present;

$Xaa_3$ represents Pro;

$Xaa_6$ represents Pro or Hyp;

$Xaa_7$, $Xaa_8$, $Xaa_9$, $Xaa_{10}$, and $Xaa_{11}$ are each optional (in which case $Xaa_6$ is bonded to $Xaa_{12}$) and are independently selected from the group Pro, Hyp, Thr, DOPA and Tyr;

and/or $Xaa_{12}$ represents Pro, Hyp, Thr, DOPA or Tyr.

Preferred compounds of the invention include those in which $Xaa_5$ represents DOPA or, more preferably Tyr;

$Xaa_3$ represents Hyp or, more preferably, Pro;

$Xaa_6$ represents diHyp or, more preferably, Hyp;

one to four of $Xaa_7$, $Xaa_8$, $Xaa_9$, and $Xaa_{10}$, are each present, each of which is selected from the group Pro, Hyp, Thr, DOPA and Tyr, and $Xaa_{11}$ is not present.

Peptide compounds of the invention that may be mentioned include those in which $Xaa_1$ represents Ser.

However, more preferred compounds of the invention include those in which $Xaa_1$ is absent or, more preferably, $Xaa_1$ represents Ala.

Preferred compounds of the invention also include those in which $Xaa_{13}$ represents Lys.

More preferably, compounds of the invention also include those in which $Xaa_{12}$ represents DOPA or Tyr, more preferably Pro or, especially, Hyp.

Preferred compounds of the invention also include those in which, when $Xaa_{13}$ represents Lys, $Xaa_{12}$ represents DOPA or Tyr, more preferably Pro or, especially, Hyp.

Further preferred compounds of the invention include those in which the amino acids in the sequence defined by $Xaa_7$, $Xaa_8$, $Xaa_9$, $Xaa_{10}$, and $Xaa_{11}$ are independently selected from Pro, preferably DOPA, more preferably Hyp, Thr and Tyr.

Especially preferred compounds of the invention include those in which, in the sequence defined by $Xaa_7$, $Xaa_8$, $Xaa_9$, $Xaa_{10}$, and $Xaa_{11}$ are each optional (in which case $Xaa_6$ is bonded to $Xaa_{12}$):

the amino acid DOPA, preferably Thr or, more preferably, Tyr is linked to $Xaa_{12}$;

the amino acid Pro, or more preferably Hyp or Thr is linked to $Xaa_6$.

Preferred values of $Xaa_7$, $Xaa_8$, $Xaa_9$, $Xaa_{10}$, and $Xaa_{11}$ include, when it is a 3-membered amino acid sequence (in which case $Xaa_{10}$ and $Xaa_{11}$ are not present), -Hyp-Thr-Tyr or, more preferably-Hyp-Thr-DOPA-, and, when it is a 2-membered amino acid sequence (in which case $Xaa_9$, $Xaa_{10}$, and $Xaa_{11}$ are not present), -Thr-Tyr- or, more preferably, -Thr-DOPA-, or -Pro-Thr- or, more preferably, -Hyp-Thr-.

Compounds of the invention that may be mentioned include those of the amino acid sequence:

Lys-Pro-Ser-Tyr-Xaa-Xaa-Thr-Xaa-Xaa-Lys (SEQ ID No: 4), where Xaa at positions 5, 6, and 9 are Hyp as defined herein and wherein Xaa at position 8 is DOPA as defined herein;

Lys-Pro-Ser-Tyr-Xaa-Xaa-Thr-Tyr-Xaa-Lys (SEQ ID No: 5), where Xaa at positions 5, 6, and 9 are Hyp as defined herein;

Lys-Pro-Ser-Tyr-Xaa-Thr-Xaa-Xaa-Lys (SEQ ID No: 6), where Xaa at positions 5 and 8 are Hyp as defined herein and wherein Xaa at position 7 is DOPA as defined herein;

and

Lys-Pro-Ser-Tyr-Xaa-Thr-Tyr-Xaa-Lys (SEQ ID No: 7), where Xaa at positions 5 and 8 are Hyp as defined herein.

Preferred compounds of the invention include those of the amino acid sequence:

Ser-Lys-Pro-Ser-Tyr-Xaa-Xaa-Thr-Xaa-Lys (SEQ ID No: 8), where Xaa at positions 6 and 7 are Hyp as defined herein and wherein Xaa at position 9 is DOPA as defined herein;

Ser-Lys-Pro-Ser-Tyr-Xaa-Xaa-Thr-Tyr-Lys (SEQ ID No: 9), where Xaa at positions 6 and 7 are Hyp as defined herein;

Ser-Lys-Pro-Ser-Tyr-Xaa-Thr-Xaa-Xaa-Lys (SEQ ID No: 10), where Xaa at positions 6 and 9 are Hyp as defined herein and wherein Xaa at position 8 is DOPA as defined herein;

Ser-Lys-Pro-Ser-Tyr-Xaa-Thr-Tyr-Xaa-Lys (SEQ ID No: 11), where Xaa at positions 6 and 9 are Hyp as defined herein.

More preferred compounds of the invention include those of the amino acid sequence:

Ala-Lys-Pro-Ser-Tyr-Xaa-Xaa-Thr-Xaa-Xaa-Lys (SEQ ID No: 12), where Xaa at positions 6, 7, and 10 are Hyp as defined herein and wherein Xaa at position 9 is DOPA as defined herein;

Ala-Lys-Pro-Ser-Tyr-Xaa-Xaa-Thr-Tyr-Xaa-Lys (SEQ ID No: 13); more preferably that defined by the amino acid sequence), where Xaa at positions 6, 7, and 10 are Hyp as defined herein:

Ala-Lys-Pro-Ser-Tyr-Xaa-Thr-Xaa-Xaa-Lys (SEQ ID No: 14), where Xaa at positions 6 and 9 are Hyp as defined herein and wherein Xaa at position 8 is DOPA as defined herein; and particularly that defined by the amino acid sequence:

Ala-Lys-Pro-Ser-Tyr-Xaa-Thr-Tyr-Xaa-Lys (SEQ ID No: 15), where Xaa at positions 6 and 9 are Hyp as defined herein.

Further compounds of the invention that may be mentioned include those in which Xaa$_{13}$ is absent, such as those of the amino acid sequence:

Lys-Pro-Ser-Tyr-Xaa-Xaa-Thr-Xaa-Xaa (SEQ ID No: 16), where Xaa at positions 5, 6, and 9 are Hyp as defined herein and wherein Xaa at position 8 is DOPA as defined herein;

Lys-Pro-Ser-Tyr-Xaa-Xaa-Thr-Tyr-Xaa (SEQ ID No: 17), where Xaa at positions 5, 6, and 9 are Hyp as defined herein;

Lys-Pro-Ser-Tyr-Xaa-Thr-Xaa-Xaa (SEQ ID No: 18), where Xaa at positions 5 and 8 are Hyp as defined herein and wherein Xaa at position 7 is DOPA as defined herein;

Lys-Pro-Ser-Tyr-Xaa-Thr-Tyr-Xaa (SEQ ID No: 19), where Xaa at positions 5 and 8 are Hyp as defined herein;

Ser-Lys-Pro-Ser-Tyr-Xaa-Xaa-Thr-Tyr (SEQ ID No: 21), where Xaa at positions 6 and 7 are Hyp as defined herein;

Ser-Lys-Pro-Ser-Tyr-Xaa-Thr-Xaa-Xaa (SEQ ID No: 22), where Xaa at positions 6 and 9 are Hyp as defined herein and wherein Xaa at position 8 is DOPA as defined herein;

Ser-Lys-Pro-Ser-Tyr-Xaa-Thr-Tyr-Xaa (SEQ ID No: 23), where Xaa at positions 6 and 9 are Hyp as defined herein;

Ala-Lys-Pro-Ser-Tyr-Xaa-Xaa-Thr-Xaa-Xaa (SEQ ID No: 24), where Xaa at positions 6, 7, and 10 are Hyp as defined herein and wherein Xaa at position 9 is DOPA as defined herein;

Ala-Lys-Pro-Ser-Tyr-Xaa-Xaa-Thr-Tyr-Xaa (SEQ ID No: 25), where Xaa at positions 6, 7, and 10 are Hyp as defined herein;

Ala-Lys-Pro-Ser-Tyr-Xaa-Thr-Xaa-Xaa (SEQ ID No: 26), where Xaa at positions 6 and 9 are Hyp as defined herein and wherein Xaa at position 8 is DOPA as defined herein;

Ala-Lys-Pro-Ser-Tyr-Xaa-Thr-Tyr-Xaa (SEQ ID No: 27), where Xaa at positions 6 and 9 are Hyp as defined herein; and particularly, that defined by the amino acid sequence:

Ser-Lys-Pro-Ser-Tyr-Xaa-Xaa-Thr-Xaa (SEQ ID No: 20), where Xaa at positions 6 and 7 are Hyp as defined herein and wherein Xaa at position 9 is DOPA as defined herein.

Further compounds of the invention in which Xaa$_1$ includes an N-terminal 3,4-dihydrocinnamic acid, include that defined by the amino acid sequence:

3,4-dihydrocinnamic acid-Ala-Lys-Pro-Ser-Tyr-Xaa-Xaa-Thr-Tyr-Lys (SEQ ID No: 28); and, more preferably, that defined by the amino acid sequence, where Xaa at positions 6 and 7 are Hyp as defined herein:

3,4-dihydrocinnamic acid-Ala-Lys-Pro-Ser-Tyr-Xaa-Thr-Tyr-Xaa-Lys (SEQ ID No: 29), where Xaa at positions 6 and 9 are Hyp as defined herein.

Further preferred compounds of the invention mentioned include those in which Xaa$_1$ is Ala and Xaa$_{13}$ is Lys, such as those of the amino acid sequence:

Ala-Lys-Pro-Ser-Xaa-Xaa-Thr-Xaa-Xaa-Lys (SEQ ID No: 30), where Xaa at positions 6 and 9 are Hyp as defined herein and wherein Xaa at positions 5 and 8 are DOPA as defined herein;

Ala-Lys-Pro-Ser-Pro-Thr-Tyr-Pro-Lys (SEQ ID No: 31);

Ala-Lys-Xaa-Ser-Tyr-Xaa-Thr-Tyr-Xaa-Lys (SEQ ID No: 32), where Xaa at positions 3, 6 and 9 are Hyp as defined herein;

Ala-Lys-Xaa-Ser-Xaa-Xaa-Thr-Xaa-Xaa-Lys (SEQ ID No: 33), where Xaa at positions 3, 6 and 9 are Hyp as defined herein and wherein Xaa at positions 5 and 8 are DOPA as defined herein; and particularly, that defined by the amino acid sequence:

Ala-Lys-Xaa-Ser-Tyr-Xaa-Thr-Xaa-Xaa-Lys (SEQ ID No: 34), where Xaa at positions 3, 6 and 9 are Hyp as defined herein and wherein Xaa at position 8 is DOPA as defined herein.

Further compounds of the invention that may be mentioned include those in which Xaa$_{13}$ is absent, such as those of the amino acid sequence:

3,4-dihydrocinnamic acid-Ala-Lys-Pro-Ser-Tyr-Xaa-Xaa-Thr-Tyr (SEQ ID No: 35), where Xaa at positions 6 and 7 are Hyp as defined herein;

3,4-dihydrocinnamic acid-Ala-Lys-Pro-Ser-Tyr-Xaa-Thr-Tyr-Xaa (SEQ ID No: 36), where Xaa at positions 6 and 9 are Hyp as defined herein;

Ala-Lys-Pro-Ser-Xaa-Xaa-Thr-Xaa-Xaa (SEQ ID No: 37), where Xaa at positions 6 and 9 are Hyp as defined herein and wherein Xaa at positions 5 and 8 are DOPA as defined herein;

Ala-Lys-Pro-Ser-Pro-Thr-Tyr-Pro (SEQ ID No: 38);

Ala-Lys-Xaa-Ser-Tyr-Xaa-Thr-Tyr-Xaa (SEQ ID No: 39), where Xaa at positions 3, 6 and 9 are Hyp as defined herein;

Ala-Lys-Xaa-Ser-Xaa-Xaa-Thr-Xaa-Xaa (SEQ ID No: 40), where Xaa at positions 3, 6 and 9 are Hyp as defined herein and wherein Xaa at position 5 and 8 are DOPA as defined herein; and Ala-Lys-Xaa-Ser-Tyr-Xaa-Thr-Xaa-Xaa (SEQ ID No: 41), where Xaa at positions 3, 6 and 9 are Hyp as defined herein and wherein Xaa at position 8 is DOPA as defined herein.

As described hereinafter, it is understood that certain compounds of the invention, including those in which, for example, Xaa$_{13}$ is Lys, and/or in which Xaa$_1$ is Ser and/or Xaa$_{12}$ is Pro or, particularly Hyp, and, in particular, compounds of the invention comprising amino acid sequences SEQ ID No: 4 to SEQ ID No: 15, and SEQ ID No: 28 to SEQ ID No: 34 are resistant to metabolism.

Nevertheless, the skilled person will appreciate that metabolites of compounds of the invention that may be formed following administration are included within the scope of the invention.

In particular, compounds of the invention in which Xaa$_{13}$ is absent, including those with amino acid sequences SEQ ID No: 16 to SEQ ID No: 27, and SEQ ID No: 35 to SEQ ID No: 41, respectively, may be formed as metabolites of corresponding compounds of the invention comprising Lys at the C-terminus, which may be cleaved from other compounds of the invention, including those with amino acid sequences SEQ ID No: 4 to SEQ ID No: 15, and SEQ ID No: 28 to SEQ ID No: 34, respectively following administration.

Nevertheless, compounds of the invention with amino acid sequences SEQ ID No: 16 to SEQ ID No: 27 and SEQ ID No: 35 to SEQ ID No: 41 are also compounds of the invention in their own right and may be made, formulated and administered to patients in exactly the same fashion as other compounds of the invention that are described herein and/or exemplified below.

For the avoidance of doubt, as used herein, Pro represents proline, Ala represents alanine, Ser represents serine, Tyr represents tyrosine, Hyp represents hydroxyproline (including 3-hydroxyproline (3Hyp) and 4-hydroxyproline (4Hyp)), diHyp represents dihydroxyproline (including 3,4-dihydroxyproline (3,4diHyp), 3,5-dihydroxyproline (3,5di- Hyp) and 4,5-dihydroxyproline (4,5diHyp)), Thr represents threonine, Lys represents lysine, Ala represents alanine and DOPA represents 3,4-dihydroxyphenylalanine. The optional 3,4-dihydrocinnamic acid residue that may be attached to $Xaa_1$ at the N-terminus is essentially a DOPA residue but without the —$NH_2$ group in the 2- or $\alpha$-carbon position relative to the carboxylic acid that is attached the N-terminus (whether Ala, Ser or Lys).

Compounds of the invention, whether in the form of salts or otherwise, include regioisomers within amino acids of the peptides (for example diHyp, Hyp and Tyr moieties), as well as mixtures of such regioisomers. For example, included within the definition of Tyr are, not only tyrosine (4-hydroxyphenylalanine), but also 2- and 3-hydroxyphenylalanine. Included within the definition of Hyp are 4-hydroxyproline (4Hyp), 3-hydroxyproline (3Hyp) and 5-hydroxyproline (5Hyp). It is more preferred that Hyp residues are 4-hydroxyproline. Similarly, included within the definition of diHyp are 3,4-dihydroxyproline (3,4diHyp), 3,5-dihydroxyproline (3,5diHyp) and 4,5-dihydroxyproline (4,5diHyp). It is more preferred that diHyp residues are 3,4-dihydroxyproline (3,4diHyp).

Also, in addition to the standard central carbon atom of the amino acids in the compounds of the invention (which are normally but not exclusively in the L-configuration), certain amino acids in the sequence comprise further chiral carbon atoms. All such stereoisomers and mixtures (including racemic mixtures) thereof are included within the scope of the invention. In respect, included within the definition of Hyp are trans-4-hydroxy-L-proline, cis-4-hydroxy-L-proline, trans-3-hydroxy-L-proline, cis-3-hydroxy-L-proline trans-5-hydroxy-L-proline and cis-5-hydroxy-L-proline, however we prefer that the Hyp that is employed in compounds of the invention is 4-hydroxy-L-proline. Similarly, corresponding definitions may be applied to diHyp, in which the two hydroxy groups can also be cis or trans relative to each other. In any event, individual enantiomers of compounds of formula I that may form part of a compound of the invention are included within the scope of the invention.

Compounds of the invention may be in the form of salts. Salts that may be mentioned include pharmaceutically-acceptable and/or cosmetically-acceptable salts, such as pharmaceutically- and/or cosmetically-acceptable acid addition salts and base addition salts. Such salts may be formed by conventional means, for example by reaction of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of active ingredient in the form of a salt with another counter-ion, for example using a suitable ion exchange resin.

Preferred salts include, for example, acetate, hydrochloride, bisulfate, maleate, mesylate, tosylate, alkaline earth metal salts, such as calcium and magnesium, or alkali metal salts, such as sodium and potassium salts. Most preferably, compounds of the invention may be in the form of acetate salts.

Compounds of the invention may be prepared by way of conventional techniques, for example by way of standard amino acid coupling techniques, using standard coupling reagents and solvents, for example as described hereinafter. Compounds of the invention may be synthesised from available starting materials using appropriate reagents and reaction conditions. In this respect, the skilled person may refer to inter alia "*Comprehensive Organic Synthesis*" by B.

M. Trost and I. Fleming, Pergamon Press, 1991. Further references that may be employed include "*Heterocyclic Chemistry*" by J. A. Joule, K. Mills and G. F. Smith, 3rd edition, published by Chapman & Hall, "*Comprehensive Heterocyclic Chemistry II*" by A. R. Katritzky, C. W. Rees and E. F. V. Scriven, Pergamon Press, 1996 and "*Science of Synthesis*", Volumes 9-17 (Hetarenes and Related Ring Systems), Georg Thieme Verlag, 2006.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention.

It will be appreciated by those skilled in the art that, in the processes described above and hereinafter, the functional groups of intermediate compounds may need to be protected by protecting groups. The protection and deprotection of functional groups may take place before or after a reaction.

Protecting groups may be applied and removed in accordance with techniques that are well-known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "Protective Groups in Organic Synthesis", 5th edition, T. W. Greene & P. G. M. Wutz, Wiley-Interscience (2014), the contents of which are incorporated herein by reference.

Compounds of the invention are useful because they possess pharmacological activity. Thus, the compounds of the invention are useful as human and animal medicine. They are therefore indicated as pharmaceuticals (and/or in veterinary science), although they may also be used as cosmetics and/or as part of a medical device.

Although compounds of the invention may possess pharmacological activity as such, certain pharmaceutically-acceptable (e.g. "protected") derivatives of compounds of the invention may exist or may be prepared which may not possess such activity, but which may be administered and thereafter be metabolised or chemically transformed to form compounds of the invention. Such compounds (which may possess some pharmacological activity, provided that such activity is appreciably lower than that of the active compounds to which they are metabolised/transformed) may therefore be described as 'prodrugs' of compounds of the invention.

As used herein, references to prodrugs will include compounds that form a compound of the invention, in an experimentally-detectable amount, within a predetermined time, following administration. All prodrugs of the compounds of the invention are included within the scope of the invention.

Compounds of the invention are particularly useful in the treatment of inflammation.

The 'treatment of inflammation' includes the treatment of inflammation in any organ of the body (including soft tissue, joints, nerves, the vascular system, internal organs, especially mucosal surfaces, and particularly the skin), irrespective of the cause, and also includes all such inflammatory disorders or conditions, and/or disorders or conditions characterized by inflammation (e.g. as a symptom).

Inflammatory disorders and/or conditions may be (and are typically) characterized by activation of immune defence mechanisms, resulting in an effect that is more harmful than beneficial to the host. Such conditions are generally associated with varying degrees of tissue redness or hyperemia, swelling, edema, hyperthermia, pain (including aching), exudation of body fluids, itching (pruritis), cell death and tissue destruction, cell proliferation, and/or loss of function.

Inflammatory conditions that may be mentioned include arteritis, diabetes mellitus, metabolic syndrome, rosacea, asthma and allergy, ankylosing spondylitis, chronic obstructive pulmonary disease, gouty arthritis, inflammatory bowel disease (such as Crohn's disease and ulcerative colitis), multiple sclerosis, osteoarthritis, pancreatitis, prostatitis, psoriatic arthritis, rheumatoid arthritis, tendinitis, bursitis, Sjogren's syndrome, systemic lupus erythematosus, uveitis, urticaria, vasculitis, mastocytosis, diabetic vascular complications, migraine, atherosclerosis and associated cardiovascular disorders. A disease state characterised by inflammation that may be mentioned is chronic obstructive pulmonary disease (COPD). A further disease state characterised by inflammation that may be mentioned is inflammatory bowel diseases including Crohn's disease and, especially, ulcerative colitis. Other disease states characterized by inflammation that may be mentioned are gynaecological diseases, such as cervicitis, vaginitis and colpitis. Diseases that affect the gastrointestinal tract, such as gastrohelcosis (e.g. gastritis, gastric ulcer, gastric cancer and other stomach mucosa diseases) as well as gastroesophageal reflux disease (GERD), constipation, and gastritis, inflammation associated with cancers and infections (e.g. viral infections, such as the common cold or influenza).

Inflammatory conditions that may be more especially mentioned include inflammations of the skin or mucosa (including the oral, nasal, ocular, vaginal, cervical and/or anorectal mucosae, more particularly the oral or nasal mucosae), such as inflammation resulting from infections (such as viral and/or bacterial infections), or allergic/atopic conditions (such as rhinitis (e.g. allergic rhinitis), pharyngitis, periodontitis, gingivitis, xerophthalmia, conjunctivitis (e.g. allergic conjunctivitis), dermatitis, urticaria (hives) and food allergy); and other inflammatory conditions, such as herpes, drug eruptions, polymorphous light eruptions, sunburn, early manifestations of skin cancers (erythema-like skin lesions), pathological hair loss (including following skin grafting), chemo rash, psoriasis, erythema multiforme, folliculitis, eczema and external otitis. A disease state that may be mentioned is polymorphous light eruptions.

More particularly, compounds may be used to treat certain conditions characterized by inflammation, and/or with which inflammation is associated. Such conditions may include wounds (including abrasions (scratches), incisions (including operative incisions), lacerations, punctures, avulsions, bruising and scarring), and burns (including inflammation resulting from surgery following burns, such as skin grafting) and other conditions, such as hemorrhoids. Wounds may be acute or chronic, and/or may result from one or more inflammatory disorders as defined herein.

Wounds of the skin or mucosa may arise from internal or external physical injury to the membrane surface, or may be caused by (i.e. be a symptom of) an underlying physiological disorder.

Physical (e.g. "open") wounds may be caused by sharp objects (cuts, incisions, punctures) or blunt objects/mechanical forces (lacerations, abrasions, avulsions), physical blows (bruises), heat or chemicals (burns and blisters), UV light (sunburn), cold (chilblains or frostbite). Wounds may be superficial (damage only to the epidermis and/or dermis) or may be full thickness wounds (damage below the epidermis and/or dermis). In serious cases, subcutaneous and/or submucosal tissues, such as muscles, bones, joints, and even internal organs, may be damaged.

Compounds of the invention may be used to relieve the pain (including aching) associated with inflammation and/or wounding. In particular, compounds of the invention may be used to relieve procedural pain and/or non-procedural pain. The skilled person will understand that the term "procedural pain" (i.e. operation pain) refers to acute pain that is associated with medical investigations and treatments conducted for the purpose of healthcare. The term "non-procedural" refers to general pain that is associated with inflammation and/or wounding (e.g. pain associated with dental ulcers, burns and/or scars), and is not a consequence of a particular medical intervention.

Compounds of the invention may be used to treat not only the inflammation, pain (including aching) and/or pruritis (itching) associated with the wound itself and the healing process, but also they may be used to prevent the exudation of body fluids from wounds, the risk of infection, and also the prevention of physiological reactions that result from inflammation and/or wound healing processes, such as scarring and melanin pigmentation.

Scarring is a consequence of inflammation and/or wound healing and is a general term for the formation of fibrotic tissue that is a consequence of such inflammation/healing.

Compounds of the invention may also be useful in the suppression of the production of melanin pigmentation, which may or may not result from inflammation and/or wound healing. Compounds of the invention may also be useful in the suppression of disorders associated with melanin pigmentation, such as chloasma, freckles, melanosis, malar rash and other chromatosis, skin cancers with melanoma, and chromatosis that is caused by exposure to the sun or skin diseases like acne.

Wounds may also arise as a consequence of (e.g. inflammatory) diseases or disorders. Such wounds may include blistering and/or ulcers of the skin and mucosa. These are common conditions that are often long-lasting and difficult to treat. Skin tissues can often be damaged, removed, liquefied, infected and/or necrotic. Ulcers can lead to secondary consequences to health particularly if they become infected, are hard to heal and are costly to treat. They can also cause significant psychological stress and economic loss to patients, affecting both general well-being and quality of life.

In the alternative, inflammatory skin conditions or diseases in which compounds of the invention find particular utility include psoriasis, acne, eczema and dermatitis, especially allergic/atopic dermatitis, as well as in the treatment of mucosal inflammation as characterized by rhinitis, especially allergic rhinitis, hemorrhoids, chronic obstructive pulmonary disease and ulcerative colitis, for example.

Psoriasis is a chronic, inflammatory skin disease with a tendency to recur (some patients never heal during their entire life). Clinical manifestations of psoriasis mainly include erythema and scales. It can occur over the whole body, but is more commonly observed on the scalp and limbs.

Acne is a follicular (pilosebaceous unit) chronic, inflammatory skin disease, the occurrence of which is closely related to main factors like hypersteatosis, blocked pilosebaceous ducts (including closed and open comedones), bacterial infection and inflammatory reactions, that tends to occur during youth, characterized by multiform skin lesions on the face. The term acne thus includes regular acne and acne rosacea (i.e. copper nose).

Eczema is a skin inflammatory reaction with strong itching caused by a variety of internal and external factors. It has three phases, acute, sub-acute, and chronic. In the acute phase, there is a tendency for the production of exudates, while the chronic phase includes infiltration and hypertrophy. Skin lesions are often itchy and recur easily.

Dermatitis is a common skin disease characterized by coarseness, redness, itching, eczema, and dryness. Small lumps, refractory ulcers, and pigmented spots caused by dermatitis may, if not treated promptly, develop to basal cell carcinoma, squamous cell carcinoma, and malignant melanoma. Dermatitis may be caused by various internal and external infectious or non-infectious factors, including substances (contact dermatitis) or allergy (allergic/atopic dermatitis). Also included is seborrheic dermatitis (seborrheic eczema) and all forms of steroid-dependent dermatitis (including light-sensitive seborrheid, perioral dermatitis, rosacea-like dermatitis, steroid-rosacea, steroid-induced rosacea, iatrosacea, steroid dermatitis resembling rosacea, topical corticosteroid-induced rosacea-like dermatitis and, more particularly, facial corticosteroid addictive dermatitis (FCAD) or facial corticosteroid-dependent dermatitis (FCDD), as characterized by flushing, erythema, telangiectasia, atrophy, papules and/or pustules in the facial area after long-term treatment with (including uncontrolled use, abuse or misuse of) topical corticosteroids; see, for example, Xiao et al, *J. Dermatol.*, 42, 697 (2015) and Lu et al, *Clin. Exp. Dermatol.*, 35, 618 (2009)).

Rhinitis is irritation and inflammation of the mucous membrane inside the nose. Common symptoms of rhinitis include a stuffy nose, runny nose, sneezing and post-nasal drip. The most common kind of rhinitis is allergic rhinitis, caused by an allergen, such as pollen, dust, mould, or flakes of skin from certain animals. It has been surprisingly found that patients with allergic rhinitis who were treated compounds of the invention experienced relief of eye itchiness, even when compounds of the invention were administered nasally (i.e. to the nasal mucosa).

Hemorrhoids are swellings caused by inflammation of the hemorrhoidal blood vessels found inside or around the rectum and the anus. Symptoms include bleeding (i.e. wounding) after the passage of a stool, prolapse of the hemorrhoid, mucus discharge and itchiness, soreness, redness and swelling in the area of the anus. Hemorrhoids are believed to be a consequence of an increase of pressure in the abdomen, for example, as a result of constipation or diarrhea.

Chronic obstructive pulmonary disease (COPD) is the name for a group of lung conditions that cause breathing difficulties, including emphysema (damage to the alveoli) and chronic bronchitis (long-term inflammation of the airways). COPD occurs when the lungs become inflamed, damaged and narrowed. The damage to the lungs is usually irreversible and results in an impairment of the flow of air into and out of the lungs. Symptoms of COPD include breathlessness, productive cough, frequent chest infections and persistent wheezing. The most common cause of the disease is smoking, although other risk factors include high levels of air pollution and occupational exposure to dust, chemicals and fumes.

Compounds of the invention may have positive effects in mitigating erythema, redness and swelling, edema, blisters, and bullous pemphigoid caused by various conditions including those mentioned generally and specifically herein, and may inhibit exudation of subcutaneous tissue fluid, and suppressing itching and pain caused by such inflammatory conditions.

Other inflammatory conditions that may be mentioned include:

(a) Mucosal inflammation, such as oral mucositis, apthhous ulcers, otitis media, laryngitis, tracheitis, esophagitis, gastritis, enteritis and enterocolitis (including bacillary dysentery, chronic amoebic dysentery, schistosomiasis, nonspecific ulcerative colitis and regional enteritis), cervicitis and endocervicitis, endometritis, inflammation caused by inhalation injury and the like, as well as mucosal inflammation associated with cancers, and infections (e.g. viral infections, such as the common cold or influenza), that affect mucosal surfaces, such as those in the oral cavity, the nasopharynx, the ear, the throat, the trachea, the gastrointestinal tract, the cervix, etc.

(b) Orthopedic inflammation associated with, for example bone fractures, pyogenic infection of bones and joints, inflammation caused by rheumatic bone diseases, as well as pyogenic osteomyelitis (acute, chronic, localized, sclerotic, post-traumatic), pyogenic arthritis; bone tumors (osteoma, osteoid osteoma, chondroma), bone cysts, (osteosarcoma, chondrosarcoma, osteoclastoma, primary bone sarcoma osteofibrosarcoma, Ewing's sarcoma, non-Hodgkin's lymphoma, myeloma, chordoma), metastatic bone tumors, tumor-like lesions of bone (bone cyst, aneurysmal bone cyst, eosinophilic granuloma, fibrous dysplasia); and rheumatic arthritis.

(c) Nerve inflammation, such as peripheral polyneuritis, facial neuritis, peripheral neuritis, subcutaneous neuritis, ulnar neuritis, intercostal neuritis, etc.

(d) Subcutaneous and submucosal soft tissue inflammation, such as myositis, ligamentitis, tendonitis, panniculitis, capsulitis, lymphadenitis, bubonadentitis, tonsillitis, synovitis, fasciitis, and soft tissue inflammation caused by injuries, contusion or laceration of muscles, ligaments, fascia, tendons, membrana synovialis, fat, articular capsules, and lymphoid tissue.

(e) Vascular inflammation, such as allergic leukocytoclastic vasculitis, allergic cutaneous vasculitis, polyarteritis nodosa, thrombotic vasculitis, granulomatous vasculitis, lymphocytic vasculitis, vasculitis with abnormalities in blood composition, and rheumatic vasculitis, as well as vascular inflammation associated with vascular cancers caused by allergic leukocytoclastic vasculitis, polyarteritis nodosa, thrombotic vasculitis, granulomatous vasculitis, lymphocytic vasculitis, vasculitis with abnormalities in blood composition, and rheumatic vasculitis.

(f) Inflammation of the internal organs, such as the heart, stomach, intestine, lung, liver, spleen, kidney, pancreas, bladder, ovary, and prostate, including but not limited to pericarditis, myocarditis, endocarditis, pneumonia, hepatitis, splenitis, nephritis pancreatitis, cystitis, oophoritis, prostatitis and treatment of gastric ulcer.

(g) Inflammation of the eye and surrounding area, such as conjunctivitis, keratitis (e.g. acute epithelial keratitis, nummular keratitis, interstitial keratitis, disciform keratitis, neurotrophic keratitis, mucous plaque keratitis, herpes simplex keratitis, herpes zoster keratitis, bacterial keratitis, fungal keratitis acanthamoebic keratitis, onchocercal keratitis, superficial punctate keratitis, ulcerative keratitis, exposure keratitis photokeratitis and contact lens acute red eye), optic neuritis, etc.

(h) Inflammation of the gums and the oral cavity, such as periodontitis, gingivitis, dental ulcers, etc.

(i) Inflammation associated with rheumatism, such as rheumatic vasculitis, rheumatoid arthritis, rheumatic bone diseases, ankylosing spondylitis, bursitis, Crohn's disease, gout, infectious arthritis, juvenile idiopathic arthritis, osteoarthritis, osteoporosis, polymyalgia rheumatica, polymyositis, psoriatic arthritis, scleroderma, Sjögren's syndrome, spondyloarthropathies, systemic lupus erythematosus, tendinitis, etc.

Compounds of the invention may also be used in the treatment of certain specific diseases of the digestive system, such as GERD, which may be characterized by an acidic taste in the mouth, regurgitation, heartburn, pain with swallowing and/or sore throat, increased salivation (water brash), nausea, chest pain, and coughing. GERD may cause injury of the esophagus, including reflux esophagitis (i.e. inflammation of the esophageal epithelium which may cause ulceration at or around the junction of the stomach and esophagus), esophageal strictures (i.e. the persistent narrowing of the esophagus caused by reflux-induced inflammation), Barrett's esophagus (i.e. intestinal metaplasia (i.e. changes of epithelial cells from squamous to intestinal columnar epithelium of the distal esophagus) and/or esophageal adenocarcinoma (a form of cancer).

Compounds of the invention may also be used in the treatment of certain specific diseases of the respiratory system, such as pulmonary cystic fibrosis, usual interstitial pneumonia, allergic pneumonia, asbestosis, emphysema, pulmonary heart disease, pulmonary embolism, etc. A specific disease state that may be mentioned in idiopathic pulmonary fibrosis (IPF).

IPF is a diffuse and fatal pulmonary interstitial disease with pathological features including alveolar epithelial damage, massive proliferation of lung fibroblasts, excessive deposition of extracellular matrix, ultimately leading to irreversible lung tissue damage. In the latter stages of the disease, subjects with IPF experience respiratory failure and death. It has been found that compounds of the invention may find utility in the treatment of IPF and/or alleviation of the symptoms associated with the disease.

Compounds of the invention are particularly useful in the treatment of the following lung and/or fibrotic conditions (whether otherwise mentioned herein or not): lung fibrosis, renal fibrosis, liver fibrosis, silicosis, acute bronchitis, chronic bronchitis, tracheobronchitis, bronchial asthma, status asthmatics, bronchiectasis, upper respiratory tract infections, including the common cold and influenza), allergic airway inflammation, bacterial pneumonia, viral pneumonia, *mycoplasma* pneumonia, reckettsia, radiaton pneumonia, pneumococcal (including staphylococcal, streptococcal and gram-negative *bacillus*) pneumonia, pulmonary candidiasis (including aspergillosis, mucormycosis, histoplasmosis, actinomycosis and nocardiosis), pulmonary mycosis, cryptococcosis, lung abscesses, anaphylactic pneumonia (Leoffer's syndrome), extrinsic allergic alveolitis, pulmonary eosinophia (eosinophilosis), obstructive pulmonary emphysema, pulmonary edema, pulmonary tuberculosis, respiratory alkalosis (acidosis), acute lung injury, interstitial lung disease, empyema, lung fibroma and cor pulmonale.

Particular mucosal disorders and disease in which compounds of the invention find utility include anorectal diseases, such as diarrhea, hemorrhoids, abscesses, fistula, fissures, anal itching, anal sinusitis, warts and rectal prolapse; inflammatory bowel disease, including Crohn's disease and, particularly, ulcerative colitis; gynaecological diseases, such as cervicitis, vaginitis, pelvic pain and disorders; and dental diseases, such as paradentitis, for example.

Compounds of the invention may further possess an antioxidation effect, by increasing SOD (superoxide dismutase) production and reducing lipid oxidation. Compounds of the invention may therefore be considered have antioxidant properties.

Compounds of the invention may also possess antipyretic properties that allow for the treatment of a fever and/or alleviate the symptoms thereof; for example, by reducing a subject's body temperature, which results in a reduction of fever. Compounds of the invention and formulations including them may therefore be considered to be antipyretics.

According to a further aspect of the invention there is provided a method of treatment of inflammation, of an inflammatory disorder, and/or of a disorder/condition characterised by inflammation (for example as a symptom), which method comprises the administration of a compound of the invention or a salt thereof to a patient in need of such treatment.

For the avoidance of doubt, in the context of the present invention, the terms "treatment", "therapy" and "therapy method" include the therapeutic, or palliative, treatment of patients in need of, as well as the prophylactic treatment and/or diagnosis of patients which are susceptible to, inflammation and/or inflammatory disorders.

Compounds of the invention may further possess antiviral properties that may allow for the treatment of a viral infection per se, that is treatment of a viral infection, or a viral disease, by interfering with the replication of the virus within a host, as opposed to the treatment of any symptoms of any viral infection or disease, such as pain and/or inflammation. Such antiviral properties may also allow for the prevention of the onset of such an infection or disease, the protection of cells in a host from (e.g. further) viral infection, prevention or arrest of the spread of viral infection or disease (within a single host, or from one host to a new host), or for the prevention of reactivation of a virus after latency in a host.

According to a further aspect of the invention there is provided a method of treatment of a viral infection, which method comprises the administration of a compound of the invention or a salt thereof to a patient in need of such treatment.

Viral infections that may be mentioned include those caused by viruses in the following families: adenoviridae (e.g. adenovirus), papillomaviridae (e.g. human papillomavirus), polyomaviridae (e.g. BK virus; JC virus), herpesviridae (e.g. herpes simplex, type 1; herpes simplex, type 2; varicella-zoster virus; Epstein-Barr virus; human cytomegalovirus; human herpes virus, type 8), poxviridae (e.g. smallpox), hepadnaviridae (e.g. hepatitis B virus), parvoviridae (e.g. parvovirus B19), astroviridae (e.g. human astrovirus), caliciviridae (e.g. norovirus; Norwalk virus), picornaviridae (e.g. coxsackievirus, hepatitis A virus; poliovirus; rhinovirus), coronoviridae (e.g. severe acute respiratory syndrome virus), flaviviridae (e.g. hepatitis C virus; yellow fever virus; dengue virus; West Nile virus; tick-borne encephalitis virus), retroviridae (e.g. human immunodeficiency virus; HIV), togaviridae (e.g. rubella virus), arenaviridae (e.g. Lassa virus), bunyaviridae (e.g. hantavirus; Crimean-Congo hemorrhagic fever virus; Hantaan virus), filoviridae (e.g. Ebola virus; Marburg virus; Ravn virus), orthomyxoviridae (e.g. influenza viruses, including influenza A virus (e.g. H1N1 and H3N2 viruses), influenza B virus or influenza C virus), paramyxoviridae (e.g. measles virus; mumps virus; parainfluenza virus, respiratory syncytial virus), rhabdoviridae (e.g. rabies virus), hepeviridae (e.g. hepatitis E virus), reoviridae (e.g. rotavirus; orbivirus; coltivirus; Banna virus), as well as viruses not assigned to families, such as hepatitis D virus.

Viruses that may be more specifically mentioned include herpes simplex, type 1 and herpes simplex, type 2 viruses, human papillomavirus, influenza virus and parainfluenza virus.

Compounds of the invention may further possess antibacterial and/or bacteriostatic properties that may allow for the treatment of a bacterial infection per se, that is treatment of a bacterial infection, or a bacterial disease, by interfering with bacterial growth or proliferation in a host, as opposed to the treatment of any symptoms of any bacterial infection or disease, such as pain and/or inflammation. Compounds of the invention may therefore be considered to be bacteriocides and/or, preferably, bacteriostatic agents.

Such antibacterial properties may also allow for the prevention of the onset of such an infection or disease, the protection of cells in a host from (e.g. further) bacterial infection, prevention or arrest of the spread of bacterial infection or disease (within a single host, or from one host to a new host), or for the prevention of reactivation of a bacterium after latency in a host.

According to a further aspect of the invention there is provided a method of treatment of a bacterial infection, which method comprises the administration of a compound of the invention or a salt thereof to a patient in need of such treatment.

As disclosed herein, compounds of the invention may further possess anticancer properties that may allow for the treatment of a cancer per se, that is treatment of a cancer by interfering with the cancer as opposed to the treatment of any symptoms of the cancer, such as pain and/or inflammation. Such anticancer properties may also include the prevention of the onset of such a disease e.g. by treating inflammation and thereby preventing such onset.

According to another aspect of the invention, there is provided a method of treatment of cancer, which method comprises the administration of a compound of the invention or a salt thereof to a patient in need of such treatment.

Particular cancers that may be mentioned include oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, skin cancer and the like caused by oral mucositis, rhinitis, otitis media, conjunctivitis, pharyngitis, laryngitis, tracheitis, esophagitis, gastritis, enterocolitis, cervicitis, endometritis, erythema-like skin lesions and the like. A particular skin cancer that may be mentioned is basal cell carcinoma.

"Patients" include reptilian, avian and, preferably, mammalian (particularly human) patients.

In accordance with the invention, compounds of the invention are preferably administered locally or systemically, for example orally, intravenously or intraarterially (including by intravascular and other perivascular devices/dosage forms (e.g. stents)), intramuscularly, cutaneously, subcutaneously, transmucosally (e.g. sublingually or buccally), rectally, intravaginally, intradermally, transdermally, nasally, pulmonarily (e.g. tracheally or bronchially), preferably topically, or by any other parenteral route, in the form of a pharmaceutical preparation comprising the compound(s) in pharmaceutically acceptable dosage form(s).

Administration by inhalation (e.g. nasally) is particularly useful when the condition to be treated is rhinitis or inflammation resulting from viral infections of the airways (e.g. upper respiratory tract infections such as the common cold and influenza).

Pulmonary administration is particularly useful when the condition to be treated is COPD or IPF. Topical forms of administration may be enhanced by creating a spray comprising active ingredients, e.g. by using a powder aerosol or by way of an aqueous mist using an appropriate atomisation technique or apparatus, such as a nebulizer.

Anorectal administration is particularly useful when the condition to be treated is hemorrhoids or ulcerative colitis, using an appropriate delivery means, such as a solution of foam to be injected or a suppository.

Administration to the lower gastrointestinal tract may also be achieved by parenteral, and particularly by peroral, delivery, by means of standard delayed- or extended-release coating techniques known to those skilled in the art. In particular, distinct parts of the upper or lower intestine may be targeted. For example, colonic administration can also be achieved by way of colon-targeted drug delivery means that are initially administered perorally or parenterally.

Compounds of the invention may in the alternative be administered by direct systemic parenteral administration. Such administration may be useful in methods of treatment of an inflammatory and/or fibrotic disorder or condition of one or more internal organs of a patient.

Internal organs that may be mentioned include the stomach, the intestines, the pancreas, the liver, the spleen, the bladder, the vascular system, the ovaries, the prostate, preferably the heart and the kidneys and more preferably the lungs.

Fibrotic conditions of internal organs that may be mentioned include acute and/or severe internal fibrotic conditions characterised by the excessive accumulation of fibrous connective tissue (as described above) in and around inflamed or damaged tissue. Formulations of the invention may thus be useful in the treatment or prevention of fibrogenesis (as described above) and the morbidity and mortality that may be associated therewith. Thus, (e.g. acute and/or severe) fibrotic conditions of the internal organs that may be treated with formulations of the invention include fibrosis of the liver, the kidneys, the lungs, the cardiovascular system, including the heart and the vascular system, the pancreas, the spleen, the central nervous system (nerve fibrosis), bone marrow fibrosis, the eyes, the vagina, the cervix, etc.

Inflammatory conditions of internal organs include any condition that is, or may develop into a condition that is, severe (i.e. one that requires intensive medical treatment), and in which some sort of inflammatory component is apparent, as may be characterised by detectable inflammation, and further in which morbidity is manifest (or is expected) and/or is life-threatening.

Inflammatory conditions that may be mentioned include one or more acute disorders or conditions of internal organs (i.e. one or more conditions that require, or may develop into a condition that requires, immediate medical interventions) that are characterized by inflammation (e.g. as a symptom), such as acute internal injuries, in one or more internal organs (including any of the organs mentioned hereinbefore). By treating such acute inflammatory disorders, formulations of the invention may prevent or arrest the development of symptoms (acute or chronic) that are associated with such conditions, and also may arrest the progress of morbidity and/or mortality that is associated with such conditions.

Acute inflammatory conditions that may be mentioned thus include conditions such as peritonitis, pancreatitis, colitis, proctitis, gastritis, duodenitis, pharyngitis, GERD, parodontitis and stomatitis. Particular acute inflammatory conditions that may be mentioned include acute injury to one or more internal organs (including any of those mentioned hereinbefore), such as acute lung injury, inhalation injury (such as burns), acute respiratory distress syndrome (ARDS), severe acute respiratory syndrome (SARS), and multiple-organ inflammation, injury and/or failure.

Such conditions may be caused by internal or external trauma (e.g. injury or a burn), or by an infection by e.g. viruses, bacteria or fungi.

For example, multiple-organ inflammation, injury and/or failure may result from extensive and/or traumatic external injuries, including traumatic and/or extensive external burns. Traumatic external burns will be understood to include second-degree, and more particularly third-degree burns and fourth-degree, burns. Extensive external burns will be understood to include burns that affect at least about 10%, such as at least about 15%, including at least about 20% of a patient's body area. External (and internal) burns may result from exposure to heat, chemicals and the like.

Acute inflammatory and/or fibrotic conditions may also result from sepsis or septic shock, which can be caused by viral, bacterial or fungal infection. Furthermore, acute lung injury, ARDS and, particularly, SARS may be caused by viruses, such as coronaviruses, include the novel SARS coronavirus 2 (SARS-COV-2).

Thus, in addition, one or more of the aforementioned (e.g. acute) inflammatory conditions may (indeed in some cases will likely) result in some form of internal tissue damage and/or dysfunction of relevant internal tissues. Relevant tissues thus include (e.g. mucosal) tissues, such as the respiratory epithelium. Such tissue damage may also give rise to one or more of the fibrotic conditions mentioned hereinbefore. For example, the SARS disease caused by the novel coronavirus SARS-CoV-2 (coronavirus disease 2019 or COVID-19) is known in many cases to result in fibrosis, which arise from one or more of a number of factors, including inflammation.

In this respect, compounds of the invention and salts thereof find particular utility in the treatment of relevant inflammatory and/or fibrotic conditions on the basis that such conditions are often characterized by one or more comorbidities. By conditions that are 'characterized by comorbidities', we include that the main condition in question results in (or from) one more further medical conditions, including (and indeed preferably) those mentioned hereinbefore, at the same time, which conditions may interact and/or overlap with each other in some way.

Thus, there are provided:

methods of treatment of at least one inflammatory and/or fibrotic disorder or condition of one or more internal organs of a patient, which method comprises direct systemic parenteral administration of a compound of the invention, or a pharmaceutically-acceptable salt thereof, to a patient in need of such treatment;

a method of treatment of two or more inflammatory and/or fibrotic disorders or conditions of one or more internal organs of a patient, which method comprises direct systemic parenteral administration of a compound of the invention, or a pharmaceutically-acceptable salt thereof, to a patient in need of such treatment; and a method of reduction in the incidence of morbidity and/or mortality that is or may be associated with one or more inflammatory and/or fibrotic disorders or conditions of one or more internal organs of a patient, which method comprises direct systemic parenteral administration of a compound of the invention, or a pharmaceutically-acceptable salt thereof, to a patient in need of such treatment.

When compounds of the invention/salts thereof administered directly and parenterally, they may be administered intravenously, intraarterially, intravascularly, perivascularly, intramuscularly, cutaneously, and/or subcutaneously, for example by way of direct injection, or by way of any other parenteral route, in the form of a compound of the invention or salt thereof in the form of a pharmaceutically-acceptable dosage form.

Pharmaceutically-acceptable formulations for use in such administration may thus comprise compounds of the invention in admixture with a pharmaceutically-acceptable adjuvant, diluent or carrier, which may be selected with due regard to the intended route of direct parenteral administration and standard pharmaceutical practice. Such pharmaceutically-acceptable carriers may be chemically inert to the active compounds and may have no detrimental side effects or toxicity under the conditions of use. Such pharmaceutically-acceptable carriers may also impart an immediate, or a modified, release of the active ingredient.

Formulations of the invention for injection may thus be in the form of an aqueous formulation such as an a suspension and/or, more preferably a solution (e.g. an (optionally) buffered aqueous formulation (e.g. solution), such as a physiological saline-containing formulation (e.g. solution), a phosphate-containing formulation (e.g. solution), an acetate-containing formulation (e.g. solution) or a borate-containing formulation (e.g. solution), or a freeze-dried powder that may be reconstituted with a vehicle, such as an aqueous vehicle prior to use (e.g. injection).

Formulations of the invention may include other suitable excipients known to those skilled in the art, such as solvents (e.g. water), co-solvents, solubilizing agents (e.g. cyclodextrins), wetting agents, suspending agents, emulsifying agents, thickening agents, chelating agents, antioxidants, reducing agents, antimicrobial preservatives, bulking agents and/or protectants.

Formulations of the invention are preferably buffered by standard techniques to physiologically-acceptable pH values (e.g. pHs of between about 4.5 and about 9.5, e.g. about 6 and about 9, such as between about 6.5 and about 8.5) using buffers and/or pH modifiers as described herein, and/or may further comprise tonicity-modifying agents (such as sodium chloride).

The above notwithstanding, preferred modes of delivery of compounds of the invention include topically to the site of inflammation (e.g. the mucosa, including the oral and/or nasal mucosa, the lung, the anorectal area and/or the colon) or, more preferably, the skin) in an appropriate (for example pharmaceutically- and topically-acceptable) vehicle suitable for application to the skin and/or the appropriate mucosal surface, and/or a commercially-available formulation, but may also include oral, intravenous, cutaneous or subcutaneous, nasal, intramuscular, intraperitoneal, or pulmonary delivery.

Administration by intradermal injection (e.g. intradermally) is particularly useful for administering the active ingredient, in the form of a solution or suspension (e.g. a dermal filler), into the dermis. This is particularly useful as a means of administration for melanin pigmentation therapy as described hereinbefore.

Compounds of the invention will generally be administered in the form of one or more for example pharmaceutical formulations in admixture with a (e.g. pharmaceutically acceptable) adjuvant, diluent or carrier, which may be selected with due regard to the intended route of administration (e.g. topical to the relevant mucosa (including the lung) or, preferably, the skin) and standard pharmaceutical or other (e.g. cosmetic) practice. Such pharmaceutically acceptable carriers may be chemically inert to the active compounds and may have no detrimental side effects or toxicity under the conditions of use. Such pharmaceutically acceptable carriers may also impart an immediate, or a modified, release of the active ingredient.

Suitable pharmaceutical formulations may be commercially available or otherwise prepared according to techniques that are described in the literature, for example, Remington *The Science and Practice of Pharmacy, 22nd* edition, Pharmaceutical Press (2012) and *Martindale—The Complete Drug Reference,* 38th Edition, Pharmaceutical Press (2014) and the documents referred to therein, the relevant disclosures in all of which documents are hereby incorporated by reference. Otherwise, the preparation of suitable formulations including compounds of the invention may be achieved non-inventively by the skilled person using routine techniques.

Compounds of the invention may be in the form of an aqueous formulation such as an emulsion, a suspension and/or a solution (e.g. an (optionally) buffered aqueous formulation (e.g. solution), such as a physiological saline-containing formulation (e.g. solution), a phosphate-containing formulation (e.g. solution), an acetate-containing formulation (e.g. solution) or a borate-containing formulation (e.g. solution), or a freeze-dried powder.

Active ingredient may further and/or in the alternative be combined with appropriate excipients to prepare:

gel formulations (for which suitable gel matrix materials include cellulose derivatives, carbomer and alginates, gummi tragacanthae, gelatin, pectin, carrageenan, gellan gum, starch, Xanthan gum, cationic guar gum, agar, noncellulosic polysaccharides, saccharides such as glucose, glycerin, propanediol, vinyl polymers, acrylic resins, polyvinyl alcohol, carboxyvinyl polymer and, particularly, hyaluronic acid);

lotions (for which suitable matrix materials include cellulose derivatives, glycerin, noncellulosic polysaccharides, polyethylene glycols of different molecular weights and propanediol);

pastes or ointments (for which suitable paste matrix materials include glycerin, vaseline, paraffin, polyethylene glycols of different molecular weights, etc.);

creams or foams (for which suitable excipients (e.g. foaming agents) include hydroxypropyl methyl cellulose, gelatin, polyethylene glycols of different molecular weights, sodium dodecyl sulfate, sodium fatty alcohol polyoxyethylene ether sulfonate, corn gluten powder and acrylamide);

powder aerosols (for which suitable excipients include mannitol, glycine, dextrin, dextrose, sucrose, lactose, sorbitol and polysorbates, e.g. a dry powder inhalant); and/or liquid, for example, water (aerosol) sprays for oral use or for inhalation (for which suitable excipients include viscosity modifiers, such as hyaluronic acid, sugars, such as glucose and lactose, emulsifiers, buffering agents, alcohols, water, preservatives, sweeteners, flavours, etc.);

injectable solutions or suspensions (which may be aqueous or otherwise and for which suitable excipients include solvents and co-solvents, solubilizing agents, wetting agents, suspending agents, emulsifying agents, thickening agents, chelating agents, antioxidants, reducing agents, antimicrobial preservatives, buffers and/or pH modifiers, bulking agents, protectants and tonicity-modifying agents). Particular injectable solutions or suspensions that may be mentioned include dermal fillers (i.e. injectable fillers or soft-tissue fillers.

Moisturizing agents, such as glycerol, glycerin, polyethylene glycol, trehalose, glycerol, petrolatum, paraffin oil, silicone oil, hyaluronic acid and salts (e.g. sodium and potassium salts) thereof, octanoic/caprylic triglyceride, and the like; and/or antioxidants, such as vitamins and glutathione; and/or pH modifiers, such as acids, bases and pH buffers, may also be included in such formulations, as appropriate. Furthermore, surfactants/emulsifiers, such as hexadecanol (cetyl alcohol), fatty acids (e.g. stearic acid), sodium dodecyl sulfate (sodium lauryl sulfate), sorbitan esters (e.g. sorbitan stearate, sorbitan oleate, etc.), monoacyl glycerides (such as glyceryl monostearate) polyethoxylated alcohols, polyvinyl alcohols, polyol esters, polyoxyethylene alkyl ethers (e.g. polyoxyethylene sorbitan monooleate), polyoxyethylene castor oil derivatives, fatty ethoxylated acid esters, polyoxylglycerides, lauryl dimethyl amine oxide, bile salts (e.g. sodium deoxycholate, sodium cholate), phospholipids, N,N-dimethyldodecylamine-N-oxide, hexadecyltrimethyl-ammonium bromide, poloxamers, lecithin, sterols (e.g. cholesterol), sugar esters, polysorbates, and the like; preservatives, such as phenoxyethanol, ethylhexyl glycerin, and the like; and thickeners, such as acryloyldimethyltaurate/VP copolymer, may be included. In particular stearic acid, glyceryl monostearate, hexadecanol, sorbitan stearate, cetyl alcohol, octanoic/capric glyceride etc. may be included, particularly in cream formulations.

Compounds of the invention, and (e.g. pharmaceutical) formulations (e.g. aqueous solutions, gels, creams, ointments, lotions, foams, pastes and/or dry powders as described above) including them, may further be combined with an appropriate matrix material to prepare a dressing or a therapeutic patch for application on a biological surface, such as the skin or a mucosal surface. Such formulations may thus be employed to impregnate a matrix material, such as gauze, non-woven cloth or silk paper. The therapeutic patch may alternatively be, for example, a band-aid, a facial mask, an eye mask, a hand mask, a foot mask, etc.

Vaseline may be employed for use in applying such dressings to wounds, but we have also found that ointments based on PEGs (e.g. PEG 400) may be combined with matrix materials to prepare dressings without the need to use vaseline.

Compounds of the invention may be administered for inhalation by way of suspension, a dry powder or a solution. Suitable inhalation devices include pressurized metered-dose inhalers (pMDIs,), which may be hand- or breath-actuated and employed with or without a standard spacer device), dry powder inhalers (DPIs), which may be single-dose, multi-dose, and power-assisted, and soft mist inhalers (SMIs) or nebulizers, in which aerosol drug in a fine mist is delivered with slower velocity than a spray delivered using, for example, a pMDI.

In pMDIs, compounds of the invention may be administered as a pressurized suspension of micronized particles distributed in a propellant (e.g. HFA, along with excipients, such as mannitol, lactose, sorbitol, etc.), or as an ethanolic solutions, to deliver one or more metered dose of between about 20 and about 100 UL with each actuation. Actuation may be effected by hand (e.g. pressing) or by inhalation (breath-actuation), involving a flow-triggered system driven by a spring In DPIs, compounds of the invention may be administered in the form of micronized drug particles (of a size between about 1 and about 5 μm), either alone or blended with inactive excipient of larger particle size (e.g. mannitol), inside a capsule, which may be pre-loaded or manually loaded into the device. Inhalation from a DPI may de-aggregate the medication particles and disperse them within the airways.

In SMIs, compounds of the invention may be stored as a solution inside a cartridge, which is loaded into the device. A spring may release the dose into a micropump, such that the dose is released when button is pressed, releasing jet streams of drug solution.

Various nebulizers may also be used to administer compounds of the invention in the form of a fine mist of aerosolized solution. Nebulizers may include breath-enhanced jet nebulizer (in which, with the assistance of a compressor, an air stream moves through jet causing drug solution to be aerosolized); breath-actuated jet nebulizers (in which, after a patient inhales, with the assistance of a compressor, an air stream moves through tube causing drug solution to be aerosolized); ultrasonic nebulizers (in which piezoelectric crystals vibrate causing aerosolization by heating causing nebulization); vibrating mesh nebulizers (in which piezoelectric crystals vibrate a mesh plate causing aerosolization to give very fine droplets without a significant change in temperature of the solution during nebulization).

According to a further aspect of the invention there is provided a process for the preparation of a pharmaceutical composition/formulation, as defined herein, which process comprises bringing into association a compound of the invention, as hereinbefore defined, with one or more pharmaceutically-acceptable excipient, as hereinbefore defined.

Compounds of the invention may also be combined in treatment with one or more growth factors selected from platelet-type growth factors (including platelet-derived growth factors, PDGFs); osteosarcoma-derived growth factors (ODGF), epidermal growth factors (EGFs), transforming growth factors (TGF$\alpha$ and TGF$\beta$), fibroblast growth factors ($\alpha$FGF, $\beta$FGF), insulin-like growth factors (IGF-I, IGF-II), nerve growth factors (NGF), interleukin-type growth factors (IL-1, IL-1, IL-3), erythropoietin (EPO), and colony stimulating factor (CSF).

According to a further aspect of the invention there is provided a (e.g. pharmaceutical) composition comprising a compound of the invention and one or more pharmaceutically-acceptable excipient, such as an adjuvant, diluent or carrier. Preferred formulations are suitable for application locally to e.g. the mucosa (including the oral and/or nasal mucosa, the lung, the anorectal area and/or the colon) or, more preferably, the skin and therefore comprise a topically-acceptable adjuvant, diluent or carrier.

There is thus further provided pharmaceutical compositions comprising compounds of the invention that are suitable for, adapted for, and/or packaged and presented for topical administration (e.g. to the mucosa, including the oral and/or nasal mucosa, the lung, the anorectal area and/or the colon, or, preferably, to the skin), as well as the use of such a formulation in the treatment of a disorder including inflammation, an inflammatory disorder and/or a condition characterized by inflammation (e.g. as a symptom) by way of direct topical administration of that formulation (e.g. to the mucosa, including the oral and/or nasal mucosa, the lung, the anorectal area and/or the colon, or, preferably, to the skin).

In relation to this aspect of the invention, for the avoidance of doubt, topical formulations comprising compounds of the invention may be used in any and all conditions described herein, including treatments of inflammation, in the treatment of any and all inflammatory disorder(s), and/or in the treatment of any and all condition(s) characterized by inflammation, as hereinbefore mentioned, defined or described. Similarly, topical formulations comprising compounds of the invention that may be mentioned include any and all of those mentioned, defined or described herein. Any and all of the relevant disclosures herein are hereby incorporated by reference in conjunction with this aspect of the invention.

Topical (e.g. liquid- or (e.g. aqueous) solution-based) formulations comprising compounds of the invention may be particularly useful in wound recovery, and may alleviate pain (including aching) and, particularly, pruritis/itching that is associated with the wound itself and the wound healing process. Such topical formulations comprising compounds of the invention may be particularly useful in the prevention and/or suppression of the exudation of body fluids from wounds, particularly during the acute inflammation stage, for example during the first 48 hours, after a burn or wound has been inflicted. This prevents the risk of infection, and other physiological reactions. Such topical formulations comprising compounds of the invention may also be particularly useful in the prevention and/or suppression of scarring and melanin pigmentation (vide supra), whether associated with wounds or otherwise.

Administration of active ingredients may be continuous or intermittent. The mode of administration may also be determined by the timing and frequency of administration, but is also dependent, in the case of the therapeutic treatment of inflammation, on the severity of the condition.

Depending on the disorder, and the patient, to be treated, as well as the route of administration, compounds of the invention may be administered at varying therapeutically effective doses to a patient in need thereof.

Similarly, the amount of active ingredient in a formulation will depend on the severity of the condition, and on the patient, to be treated, but may be determined by the skilled person.

In any event, the medical practitioner, or other skilled person, will be able to determine routinely the actual dosage, which will be most suitable for an individual patient, depending on the severity of the condition and route of administration. The dosages mentioned herein are exemplary of the average case; there can, of course, be individual instances where higher or lower dosage ranges are merited, and such are within the scope of this invention.

Doses may be administered between once and four (e.g. three) times daily.

Appropriate concentrations of compounds of the invention in an aqueous solution product may be about 0.01 (e.g. about 0.1) to about 15.0 mg/mL, in all cases calculated as the free (non-salt) compound.

Appropriate topical doses of compounds of the invention are in the range of about 0.05 to about 50 $\mu$g/cm$^2$ of treated area, such as about 0.1 (e.g. about 0.5) to about 20 $\mu$g/cm$^2$ of treated area, including about 1 to about 10 $\mu$g/cm$^2$) of treated area, such as about 5 $\mu$g/cm$^2$ of treated area, in all cases calculated as the free (non-salt) compound.

Appropriate doses of compounds of the invention for nasal administration (e.g. by inhalation) are in the range of about 0.01 $\mu$g to about 2000 mg, for example between about 0.1 $\mu$g to about 500 mg, or between 1 $\mu$g to about 100 mg. Particular doses for nasal administration that may be mentioned include between about 10 $\mu$g to about 1 mg, particularly a dose of about 0.1 mg (i.e. about 100 $\mu$g). Nasal administration of about 0.1 mg per day of compounds of the invention has been found to be particularly effective in the treatment of conditions associated with inflammation of the nasal passages and mucosae, such as rhinitis (e.g. allergic rhinitis).

Appropriate doses of compounds of the invention for pulmonary administration (e.g. by inhalation) are in the range of about 0.01 μg to about 2000 mg, for example between about 0.1 μg to about 500 mg, or between 1 μg to about 100 mg. Particular doses for pulmonary administration that may be mentioned include between about 10 μg to about 10 mg, particularly a dose of about 0.6 mg (i.e. 60 μg) to 6 mg (e.g. for use in treating COPD or IPF).

We prefer that pH values of formulations comprising compounds of the invention are in the range of about 1.0 to about 9.0 (for example about 3.0 to about 8.0).

In any event, the dose administered to a mammal, particularly a human, in the context of the present invention should be sufficient to effect a therapeutic response in the mammal over a reasonable timeframe (as described hereinbefore). One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease, as well as genetic differences between patients.

In the uses and methods described herein, compounds of the invention may also be combined with one or more active ingredients that are useful in the treatment of inflammation and/or inflammatory disorders (other anti-inflammatory agents). Such patients may thus also (and/or already) be receiving therapy based upon administration of one or more of such other active ingredients, by which we mean receiving a prescribed dose of one or more of those active ingredients mentioned herein, prior to, in addition to, and/or following, treatment with a compound of the invention.

Such anti-inflammatory agents that may be used in combination with compounds of the invention in the treatment of inflammation include therapeutic agents that are useful in the treatment of inflammation and/or of diseases characterized by inflammation as one of its symptoms. Depending on the condition to be treated, such anti-inflammatory agents may include NSAIDS (e.g. aspirin), leukotriene receptor antagonists (e.g. montelukast), corticosteroids, analgesics and certain enzymes, such as trypsin, for example as described hereinafter. Compounds of the invention may also be combined with leukotriene B4 (LTB4).

In this context, compounds of the invention may also be combined for use in the treatment of inflammation with one or more mussel adhesive proteins (MAPs), which includes any adhesive protein that may be derived from mussel species, such as *Mytilus edulis* (blue mussel), including full length proteins, including all sub-types, that are or may be derived from mussels, such as the collagens pre-COL-P, pre-COL-D and pre-COL-NG, the mussel feet matrix proteins PTMP and DTMP, and, more preferably, mfps or mefps, such as mefp-2, mefp-3, mefp-4, mefp-5, mefp-6 and especially mefp-1, and includes mixtures or combinations of any of these proteins, such as mefps. Naturally-occurring MAPs may be prepared, for example by mixed adsorption chromatography (see Chinese Patent No. ZL200710179491.0), by carboxymethyl ion exchange chromatography (see Chinese Patent No. ZL200710179492.5), and/or by salting out and dialysis (Chinese Patent No. ZL200910087567.6). Commercial sources of MAPs include USUN Bio Co. (China; sold as MAP Medical Device®), BD Biosciences (USA), Kollodis (South Korea) and Biopolymer (Sweden). MAPs may alternatively be produced using known recombinant DNA methods.

Derivatives (e.g. pharmaceutically-acceptable derivatives) of MAPS may also be combined with compounds of the invention and include compounds with, for example, molecular weights in the range of about 500 Da to about 2,000 Da (e.g. about 1,500, such as about 1,200, including about 800 Da). Such derivatives may also include other compounds that comprise amino acid sequences that are the same as, or are (e.g. minor) variants (as hereinbefore defined) of, sequences that have been identified in naturally-occurring MAPs, and which may be synthesized by chemical and/or biological processes (e.g. chemical modifications of naturally-occurring MAPS, or direct synthesis).

For example, as discussed hereinbefore, the isolated decapeptide compounds of the sequences:

Ala-Lys-Pro-Ser-Tyr-Xaa-Xaa-Thr-Xaa-Lys (mefp-1 decapeptide, SEQ ID No: 1), where Xaa at positions 6 and 7 are hydroxyproline (Hyp) and Xaa at position 9 is 3,4-dihydroxyphenylalanine (DOPA); and Ala-Lys-Pro-Ser-Tyr-Xaa-Xaa-Thr-Tyr-Lys (SEQ ID No: 2), where Xaa at positions 6 and 7 represents hydroxyproline (Hyp);

are pharmaceutically-acceptable low molecular weight derivatives of MAP that may be combined with a compound of the invention.

Other preferred agents that may be combined with compounds of the invention include LTB4 (to treat wounds and burns), NSAIDS (e.g. aspirin) or montelukast (to treat inflammation generally) and trypsin (to treat inflammation of the mucosa associated with e.g. viral infections).

Compounds of the invention may also be combined with other therapeutic agents which, when administered, are known to give rise to inflammation as a side-effect.

When compounds of the invention may be "combined" with other therapeutic agents in this way, the active ingredients may be administered together in the same formulation, or administered separately (simultaneously or sequentially) in different formulations.

Such combination products provide for the administration of compounds of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:

(1) a pharmaceutical formulation including a compound of the invention; another anti-inflammatory agent, or agent known to give rise to inflammation as a side-effect; and a pharmaceutically-acceptable excipient (e.g. adjuvant, diluent or carrier), which formulation is hereinafter referred to as a "combined preparation"; and (2) a kit of parts comprising components:

(A) a pharmaceutical formulation including a compound of the invention in admixture with a pharmaceutically-acceptable adjuvant, diluent or carrier; and (B) a pharmaceutical formulation including another anti-inflammatory agent, or agent known to give rise to inflammation as a side-effect, in admixture with a pharmaceutically-acceptable adjuvant, diluent or carrier, which components (A) and (B) are each provided in a form that is suitable for administration in conjunction with the other.

In a further aspect of the invention, there is provided a process for the preparation of a combined preparation as hereinbefore defined, which process comprises bringing into association a compound of the invention, the other antiinflammatory agent, or agent known to give rise to inflammation as a side-effect, and at least one (e.g. pharmaceutically-acceptable) excipient.

In a further aspect of the invention, there is provided a process for the preparation of a kit-of-parts as hereinbefore defined, which process comprises bringing into association components (A) and (B). As used herein, references to bringing into association will mean that the two components are rendered suitable for administration in conjunction with each other.

Thus, in relation to the process for the preparation of a kit-of-parts as hereinbefore defined, by bringing the two components "into association with" each other, we include that the two components of the kit-of-parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Thus, there is further provided a kit of parts comprising:

(I) one of components (A) and (B) as defined herein; together with (II) instructions to use that component in conjunction with the other of the two components.

The kits of parts described herein may comprise more than one formulation including an appropriate quantity/dose of a compound of the invention, and/or more than one formulation including an appropriate quantity/dose of another anti-inflammatory agent, in order to provide for repeat dosing. If more than one formulation (comprising either active compound) is present, such formulations may be the same, or may be different in terms of the dose of either compound, chemical composition(s) and/or physical form(s).

With respect to the kits of parts as described herein, by "administration in conjunction with", we include that respective formulations comprising a compound of the invention and other anti-inflammatory agent are administered, sequentially, separately and/or simultaneously, over the course of treatment of the relevant condition.

Thus, in respect of the combination product according to the invention, the term "administration in conjunction with" includes that the two components of the combination product (compound of the invention and other anti-inflammatory agent) are administered (optionally repeatedly), either together, or sufficiently closely in time, to enable a beneficial effect for the patient, that is greater, over the course of the treatment of the relevant condition, than if either a formulation comprising compound of the invention, or a formulation comprising the other agent, are administered (optionally repeatedly) alone, in the absence of the other component, over the same course of treatment. Determination of whether a combination provides a greater beneficial effect in respect of, and over the course of treatment of, a particular condition will depend upon the condition to be treated or prevented, but may be achieved routinely by the skilled person.

Further, in the context of a kit of parts according to the invention, the term "in conjunction with" includes that one or other of the two formulations may be administered (optionally repeatedly) prior to, after, and/or at the same time as, administration of the other component. When used in this context, the terms "administered simultaneously" and "administered at the same time as" include that individual doses of the relevant compound of the invention and other anti-inflammatory agent are administered within 48 hours (e.g. 24 hours) of each other.

In a further aspect of the invention, there is provided a process for the preparation of a combined preparation as hereinbefore defined, which process comprises bringing into association a compound of the invention or a salt thereof, as hereinbefore defined, the other anti-inflammatory agent, or agent known to give rise to inflammation as a side-effect, and at least one pharmaceutically-acceptable excipient.

Certain compounds of invention may in addition to, and/or instead of, possessing the aforementioned biological activity, possess adhesive properties.

Such compounds of the invention may adhere to a number of substrates including inorganic substrates, such as glass, metal and the like, as well as organic substrates, such as biological tissue.

In respect, such compounds of the invention may also be used as wound surface repair products, wound surface protecting products, medical biological adhesive products, medical coating products, industrial coating products (e.g. in corrosion prevention in ships, electronic apparatuses, pipelines and the like), biochemical reagents, medical products, sterilization products, culture vessels for cell culture and the like.

Such compounds of the invention may form a film over various skin and mucous wound surfaces such as burns, scalds, ulcers, chilblains and bedsores to aid in recovery. Such compounds of the invention may also be used in surgery, e.g. in the closure of surgical incisions, adhesion of fractured bones, adhesion of mucous membranes, coatings of human body implants such as artificial bones, cartilage brackets, periostea, artificial joints, dental implants, plugging stents, spinal fusion devices, spinal spacers and organ patches.

According to a further aspect of the invention, there is provided a compound of the invention or a salt thereof as an adhesive or a film-forming material.

Wherever the word "about" is employed herein, for example in the context of amounts, such as concentrations and/or doses of active ingredients, molecular weights or pHs, it will be appreciated that such variables are approximate and as such may vary by ±10%, for example ±5% and preferably ±2% (e.g. ±1%) from the numbers specified herein. In this respect, the term "about 10%" means e.g. ±10% about the number 10, i.e. between 9% and 11%.

Compounds of the invention have the advantage that they may be used in variety of conditions characterised by inflammation, whether that condition is an organic inflammatory disease per se or is associated with, or is characterised by, inflammation (e.g. a wound, a burn or a viral infection).

Compounds of the invention may also have the advantage that they demonstrate improved resistance to in vivo metabolism compared to compounds described in the prior art, including those defined by SEQ ID: No. 1 and/or SEQ ID: No. 2. Compounds of the invention may demonstrate improved resistance to metabolism by chymotrypsin (a digestive enzyme that breaks down proteins) and/or elastase (an enzyme that breaks down elastin which, together with collagen, determines the mechanical properties of connective tissue.

The compounds, uses and methods described herein may also have the advantage that, in the treatment of the conditions mentioned hereinbefore, they may be more convenient for the physician and/or patient than, be more efficacious than, be less toxic than, have a broader range of activity than, be more potent than, produce fewer side effects than, or that it/they may have other useful pharmacological properties over, similar compounds or methods (treatments) known in the prior art, whether for use in the treatment of inflammation, inflammatory disorders, or disorders characterised by inflammation as a symptom (including wounds), or otherwise.

The invention is illustrated by the following examples, in which, FIG. 1 shows Evans blue content in rectal and anal tissue indicating vascular permeability of test compounds.

EXAMPLES

Example 1

```
                              (SEQ ID No: 15)
     Ala-Lys-Pro-Ser-Tyr-Hyp-Thr-Tyr-Hyp-Lys
```

Fmoc-Lys-Boc-Wang resin (9.15 g, GLS180322-41301. GL Biochem. Shanghai, China) was loaded into a glass reaction column.

Methylene chloride (DCM, 200 mL; Shandong Jinling Chemical Industry Co Ltd, Shandong, China) was added to the column and allowed to soak the resin for about half an hour. The DCM was then removed by vacuum filtration.

The resin was washed 3 times with N,N-dimethylformamide (DMF, 200 mL; Shandong shitaifeng Fertilizer Industry Co Ltd, Shandong, China).

A 20% piperidine solution in DMF (200 mL) and was added as deprotection solution and reacted for 20 minutes. The solution was then removed by vacuum filtration and the column was washed with DMF six times. Fmoc-4-Hyp (tBu)-OH (GLS 21303; GL Biochem, Shanghai, China) and 2-(1H-benzotriazole-1-yl)-1,1,3,3-tetramethylaminium tetrafluoroborate (TBTU, 2.89 g; GLS 170805-00705. GL Biochem, Shanghai, China) were added to the resin. DMF (150 mL) was added to the reaction column, followed by N,N-diisopropylethylamine (DIPEA, 2.33 g; Suzhou Highfine Biotech Co. Ltd, Jiangsu, China). A colour reaction was detected in the resin after 30 minutes, indicating the reaction was complete. The solvent was removed by vacuum filtration.

The above coupling steps were repeated to couple the remaining amino acids in the same amounts (by mols): Fmoc-Tyr (tBu)-OH, Fmoc-Thr (tBu)-OH, Fmoc-4-Hyp (tBu)-OH, Fmoc-Tyr (tBu)-OH, Fmoc-Ser (tBu)-OH, Fmoc-Pro-OH, Fmoc-Lys (Boc)-OH and Fmoc-Ala-OH.

91.5 mL (i.e. 10 mL per gram of resin) of lysate, which comprised of 95% trifluoroacetic acid (TFA), 2.5% water and 2.5% triisopropylsilane (Tis), was added to immerse the resin-bounded peptide compound. The side chains were also deprotected during cleavage. After cleavage the solid support was removed by filtration and the filtrate is concentrated under reduced pressure. The cleaved peptide was precipitated with diethyl ether and lyophilized to yield crude title compound.

1 mg of crude product was dissolved in 1 mL of an acetonitrile and water mixture (1:3) and detected using a P3000A HPLC pump and LC3000 semi-preparation equipment (preparation column model: GS-120-10-C18-AP 30 mm; Beijing Chuangxintongheng Science & Technology Co., Ltd., Beijing, China). The appropriate gradient for elution was calculated and the target peak was detected at 11.035 with LCMS (analysis column model: GS-120-5-C18-BIO, 4.6*250 mm; detection: UV at 220 nm; solvent A: 0.1% TFA in MeCN, solvent A: 0.1% TFA in water; flow rate 1.0 mL/min.; volume: 10 μL).

The crude compound was desalted using an anion exchange resin, analysed and freeze-dried. Purified peptide was obtained after purification.

The synthesis described above was repeated, with the exception that, after Fmoc-Ala-OH was coupled to the resin, a deprotection step was carried out to remove the Fmoc group, and the resin was washed 3 times with DMF (200 mL).

A 20% piperidine solution in DMF (200 mL) was added as a deprotection solution and reacted for 20 minutes. Then, the resin was washed three times each with the following solvents, DMF (200 mL), DCM (200 mL) and methanol (200 ml; Xilong Scientific Co., Ltd., Guangdong, China). The resin was dried under vacuum for about 2 hours.

85.0 mL (i.e. 10 mL per gram of the dried resin) of lysate was added to immerse the resin-bounded peptide-containing compound. After cleavage for about 2 hours the solid support was removed by filtration and the filtrate was collected under reduced pressure. The filtrate was precipitated with 850 ml (i.e. 10 mL per ml of the filtrate) of diethyl ether (Xilong Scientific Co., Ltd., Guangdong, China) and the sediment was collected by filtration. The sediment was dried by vacuum for about 2 hours, yielding 3.66 g of crude title compound.

The crude product was firstly analyzed as a 1 mg/ml sample in pure water and detected using a Shimadzu LCMS-8050 system. The analysis column was an Angilent ZORBAX Eclipse SB-C18 (4.6×250 mm, 5 μm column; detection: UV at 220 nm; solvent A: 0.1% TFA in MeCN, solvent B: 0.1% TFA in water, with a linear gradient from 5%~90% solvent A concentration in 50 minutes; flow rate 1.0 mL/min; sample volume: 10 μL).

The target peak was eluted at 9.537 minutes and had the expected molecular weight, with a purity of 77.256%. MS: m/z 1183.1

3.6 g of crude product was then dissolved in 40 ml of pure water and purified using LC3000 semi-preparation equipment. The preparation column model was a Dubhe-C18 model (Hanbon Sci. & Tech. Co., Ltd., Jiangsu, China) (50*250 mm column; detection: UV at 220 nm). The appropriate gradient for elution was calculated from LCMS detection step (Solvent A: 0.1% TFA in MeCN, solvent B: 0.1% TFA in water, with a linear gradient from 5%~20% solvent A concentration in 30 minutes; flow rate 60.0 mL/min;). Fractions were collected and analyzed using a Shimadzu LC-20 HPLC system (column as above, except with a linear gradient from 5%~30% solvent A concentration in 25 minutes).

Fractions with a purity of 98% were then mixed together for an anion exchange step. This was achieved using a LC3000 semi-preparation equipment (preparation column model: Dubhe-C18 model (as above). The fractions were diluted once with pure water and loaded to the column directly, after that the column was washed with 0.37% of ammonium acetate in pure water for about 20 minutes at the flow rate of 60 mL/min, then eluted with the following gradient (Solvent A: 0.1% HAC in MeCN, solvent B: 0.1% HAc in water, with a linear gradient from 5%~20% solvent A concentration in 30 minutes; flow rate 60.0 mL/min). Fractions were collected and analyzed using Shimadzu LC-20 HPLC system (column and conditions as above).

Fractions with a purity of 98% were mixed and freeze-dried to give 2.03 g of the purified title compound.

Example 2

Croton Oil-Induced Anal Swelling Model in Rats

A gel comprising 0.5 g of the peptide Ala-Lys-Pro-Ser-Tyr-Hyp-Thr-Tyr-Hyp-Lys (SEQ ID No: 15; see Example 1 above) was made, which also consisted of the following components: methyl cellulose (2.2 g; Shandong Guangda Technology Development Co., Ltd., ShanDong, China), glycerin (11 g) and propanediol 11 g (both Sinopharm Chemical Reagent Co. Ltd.), and purified water (75.3 g).

The methyl cellulose and water were mixed together and stirred until to a homogeneous colloidal suspension was formed. Then, the peptide powder, glycerin and propanediol were added to the methyl cellulose/water mixture, and the resultant mixture quickly stirred for 5 minutes to obtain the finished product.

6-8 weeks old SD rats with average body weights of between 180 and 220 g were supplied by Changzhou Cvens Experimental Animal Co. Ltd (Changzhou, Jiangsu Province, China), half male and half female. Prior to any experiments being conducted, rats were housed under standardized conditions (at a constant temperature or 22±2° C., with alternating 12-hour periods of light and darkness) and were fed on a standard rat diet with water, for about a week.

32 rats were randomly divided into 4 groups with 8 rats in each group.

Rats were anesthetized by isoflurane (China Pharmaceutical Group Chemical Reagents Co., Ltd) inhalation. A 75% alcohol cotton ball was used to disinfect the skin around the anus. 0.16 mL of croton oil mixture (one part distilled water, four parts of pyridine (Nanjing Chemical Reagent Co., Ltd), five parts ether (China Pharmaceutical Group Chemical Reagents Co., Ltd) and ten parts 6% croton oil (Shanghai Yuanye Biotechnology Co., Ltd) was dripped slowly onto the cotton swab, and inserted into the rat anus for 0.5 cm.

The rat was lifted the rat to keep the head upwards (maintaining for 10 seconds), then the cotton swab was withdrawn and the croton oil mixture evenly applied to the surrounding skin. The blank control group was given the same volume of olive oil.

One hour after modeling, rats in each group were treated as follows:

control group—given normal saline ('Control'), model' group—treated with a blank gel with no active ingredients ('Model'), positive control—MaYinglong hemorrhoids ointment (MaYinglong Pharmaceutical Group Co., Ltd.; 'Mayinglong')·

Peptide Gel (as above; 'Peptide')

200 μL of test substances were drawn with 1 ml syringe (with the needle removed). The syringe was inserted into the anal canal and about 160 ml of the respective test substances were pushed to about 1.5 cm in depth. The remaining drug was applied to the surrounding skin near the anus. The skin around the anus was held tightly for about 1 minute to prevent drug discharge.

In the morning of the fourth day, 1% Evans blue (EB) was injected into the tail vein 30 minutes after drug administration (200 μL/100 g). The rats were the sacrificed by cervical dislocation after another 30 minutes.

The rats were place in the supine position on an anatomical plate and their abdomens were opened. The rectoanal tissues (15 mm in length) were isolated and weighed and the EB dye present in the tissue was extracted using 1 mL of formamide.

All samples were transferred to a 55° C. water bath or a heat block. Incubation for 24 hours extracted EB from the tissue. The formamide/EB mixture was centrifuged to pelletize any remaining tissue fragments. Absorbance was measured at 610 nm, using 500 μL of formamide as a blank.

The content of EB in rectal and anal tissues was calculate using amount (in ng) of EB extravasated per mg of tissue to evaluate vascular permeability. The results are shown in FIG. 1 and show that the test peptide may reduce inflammatory swelling caused by croton oil application.

Example 3

(SEQ ID No: 14)
Ala-Lys-Pro-Ser-Tyr-Hyp-Thr-DOPA-Hyp-Lys

The title compound of SEQ ID NO: 14 was prepared using essentially the same process as the latter one described in Example 1 above, except that Fmoc-DOPA (Acetonide)-OH was used instead of Fmoc-Tyr (tBu)-OH in the relevant amino acid coupling step to yield 3.73 g of crude title compound.

Analysis showed a target peak that was eluted at 9.297 minutes with the expected molecular weight (MS: m/z 1199.1). The purity was 74.493%.

3.7 g of the crude product was then purified as described in Example 1 above to give 2.01 g of pure title compound after freeze-drying.

Example 4

3,4-dihydrocinnamic acid-Ala-Lys-Pro-Ser-Tyr-Hyp-Thr-Tyr-Hyp-Lys (SEQ ID No: 29)

The title compound of SEQ ID NO: 29 was prepared using essentially the same process as the latter one described in Example 1 above, except that a final coupling with 3,4-dihydroxyhydrocinnamic acid was performed to yield 4.05 g of crude title compound.

Analysis showed a target peak that was eluted at 9.716 minutes with the expected molecular weight (MS: m/z 1347.1). The purity was 79.183%.

4.0 g of the crude product was then purified as described in Example 1 above to give 2.67 g of pure title compound after freeze-drying.

Example 5

Ala-Lys-Hyp-Ser-Tyr-Hyp-Thr-DOPA-Hyp-Lys (SEQ ID No: 34)

The title compound of SEQ ID NO: 34 was prepared using essentially the same process as the latter one described in Example 1 above, except that Fmoc-DOPA (acetonide)-OH and Fmoc-4-Hyp (tBu)-OH were used instead of Fmoc-Tyr (tBu)-OH and Fmoc-Pro-OH, respectively, in the relevant amino acid coupling steps to yield 3.79 g of crude title compound.

Analysis showed a target peak that was eluted at 9.177 minutes with the expected molecular weight (MS: m/z 1215.7). The purity was 75.365%.

3.7 g of the crude product was then purified as described in Example 1 above to give 2.09 g of pure title compound after freeze-drying.

Example 6

Synthesis of Other Peptides

The following peptides were synthesised according to essentially the same processes as those described in Example 1 above, except that appropriate amino acids were used in the appropriate peptide coupling sequences:

```
                              (SEQ ID No: 4; MS: m/z 1241.3)
Lys-Pro-Ser-Tyr-Hyp-Hyp-Thr-DOPA-Hyp-Lys;

(SEQ ID No: 5; MS: m/z 1225.3)
Lys-Pro-Ser-Tyr-Hyp-Hyp-Thr-Tyr-Hyp-Lys;

(SEQ ID No: 6; MS: m/z 1128.2)
Lys-Pro-Ser-Tyr-Hyp-Thr-DOPA-Hyp-Lys;

(SEQ ID No: 7; MS: m/z 1112.2)
Lys-Pro-Ser-Tyr-Hyp-Thr-Tyr-Hyp-Lys;

(SEQ ID No: 8; MS: m/z 1215.3)
Ser-Lys-Pro-Ser-Tyr-Hyp-Hyp-Thr-DOPA-Lys;

(SEQ ID No: 9; MS: m/z 1199.3)
Ser-Lys-Pro-Ser-Tyr-Hyp-Hyp-Thr-Tyr-Lys;

(SEQ ID No: 10; MS: m/z 1215.3)
Ser-Lys-Pro-Ser-Tyr-Hyp-Thr-DOPA-Hyp-Lys;

(SEQ ID No: 11; MS: m/z 1199.3)
Ser-Lys-Pro-Ser-Tyr-Hyp-Thr-Tyr-Hyp-Lys;

(SEQ ID No: 12; MS: m/z 1312.4)
Ala-Lys-Pro-Ser-Tyr-Hyp-Hyp-Thr-DOPA-Hyp-Lys;

(SEQ ID No: 13; MS: m/z 1296.4)
Ala-Lys-Pro-Ser-Tyr-Hyp-Hyp-Thr-Tyr-Hyp-Lys;

(SEQ ID No: 16; MS: m/z 1113.1)
Lys-Pro-Ser-Tyr-Hyp-Hyp-Thr-DOPA-Hyp;

(SEQ ID No: 17; MS: m/z 1097.1)
Lys-Pro-Ser-Tyr-Hyp-Hyp-Thr-Tyr-Hyp;

(SEQ ID No: 18; MS: m/z 1000)
Lys-Pro-Ser-Tyr-Hyp-Thr-DOPA-Hyp;

(SEQ ID No: 19; MS: m/z 984)
Lys-Pro-Ser-Tyr-Hyp-Thr-Tyr-Hyp;

(SEQ ID No: 20; MS: m/z 1087.1)
Ser-Lys-Pro-Ser-Tyr-Hyp-Hyp-Thr-DOPA;

(SEQ ID No: 21; MS: m/z 1071.1)
Ser-Lys-Pro-Ser-Tyr-Hyp-Hyp-Thr-Tyr;

(SEQ ID No: 22; MS: m/z 1087.1)
Ser-Lys-Pro-Ser-Tyr-Hyp-Thr-DOPA-Hyp;

(SEQ ID No: 23; MS: m/z 1071.1)
Ser-Lys-Pro-Ser-Tyr-Hyp-Thr-Tyr-Hyp;

(SEQ ID No: 24; MS: m/z 1184.2)
Ala-Lys-Pro-Ser-Tyr-Hyp-Hyp-Thr-DOPA-Hyp;

(SEQ ID No: 25; MS: m/z 1168.2)
Ala-Lys-Pro-Ser-Tyr-Hyp-Hyp-Thr-Tyr-Hyp;

(SEQ ID No: 26; MS: m/z 1071.1)
Ala-Lys-Pro-Ser-Tyr-Hyp-Thr-DOPA-Hyp;

(SEQ ID No: 27; MS: m/z 1055.1)
Ala-Lys-Pro-Ser-Tyr-Hyp-Thr-Tyr-Hyp;
```

32

```
-continued
and (SEQ ID No: 30; MS: m/z 1215.3)
Ala-Lys-Pro-Ser-DOPA-Hyp-Thr-DOPA-Hyp-Lys
```

The following peptides are synthesised according to essentially the same processes as those described in Example 1 above, except that appropriate amino acids were used in the appropriate peptide coupling sequences:

```
                              (SEQ ID No: 28)
3,4-dihydrocinnamic acid-Ala-Lys-Pro-Ser-Tyr-
Hyp-Hyp-Thr-Tyr-Lys;

(SEQ ID No: 32)
Ala-Lys-Hyp-Ser-Tyr-Hyp-Thr-Tyr-Hyp-Lys;
and (SEQ ID NO: 33)
Ala-Lys-Hyp-Ser-DOPA-Hyp-Thr-DOPA-Hyp-Lys.
```

Example 7

Cream Formulations I

Cream-based formulations comprising each of the peptides Lys-Pro-Ser-Tyr-Hyp-Hyp-Thr-DOPA-Hyp-Lys (SEQ ID No: 4); Lys-Pro-Ser-Tyr-Hyp-Hyp-Thr-Tyr-Hyp-Lys (SEQ ID No: 5); Lys-Pro-Ser-Tyr-Hyp-Thr-DOPA-Hyp-Lys (SEQ ID No: 6); and Lys-Pro-Ser-Tyr-Hyp-Thr-Tyr-Hyp-Lys (SEQ ID No: 7) (see Example 6 above), were made as follows using the following excipients, all of which were sourced from Sinopharm Chemical Reagent Co. Ltd, Shanghai, China.

Sorbitan stearate (0.6 g), polysorbate-80 (1 g), silicone oil (0.5 g), hexadecanol (2 g), octanoic acid/decanoic acid glyceride (5 g), liquid paraffin (2 g), monostearate glyceride (2 g) and vaseline (5 g) were mixed together and stirred. The mixture was heated to 85° C. until the mixture had completely melted.

Methyl cellulose (0.5 g), glycerin (4 g), trehalose (0.5 g) and 64.97 g of purified water, were mixed together, stirred and heated to 85° C. to form a homogeneous colloidal suspension.

30 mg of each of the four peptides were dissolved in 1 g of purified water.

The copolymer/water mixture was added to the sorbitan stearate-containing mixture, which was then quickly stirred using emulsification equipment for 5 minutes. The resultant emulsion was cooled to 55° C., and then polyethylene glycol 200 (4 g), phenoxy alcohol (0.3 g) and ethylhexyl glycerin (0.1 g) were added to the mixture with constant stirring until a uniform suspension was obtained. Then, the solution containing Lys-Pro-Ser-Tyr-Hyp-Hyp-Thr-DOPA-Hyp-Lys (SEQ ID No: 4) was mixed in.

The resultant mixture was allowed to cool to room temperature to obtain the finished product.

This procedure was repeated for the other three peptides. Further, essentially the same procedure as that described above was employed to make cream-based formulations comprising 100 mg each of Ser-Lys-Pro-Ser-Tyr-Hyp-Hyp-Thr-DOPA-Lys (SEQ ID No: 8); Ser-Lys-Pro-Ser-Tyr-Hyp-Hyp-Thr-Tyr-Lys (SEQ ID No: 9); Ser-Lys-Pro-Ser-Tyr-Hyp-Thr-DOPA-Hyp-Lys (SEQ ID No: 10); and Ser-Lys-Pro-Ser-Tyr-Hyp-Thr-Tyr-Hyp-Lys (SEQ ID No: 11) (see Example 6 above)

Example 8

Cream Formulations II

Cream-based formulations comprising each of the peptides Ala-Lys-Pro-Ser-Tyr-Hyp-Hyp-Thr-DOPA-Hyp-Lys (SEQ ID No: 12); Ala-Lys-Pro-Ser-Tyr-Hyp-Hyp-Thr-Tyr-Hyp-Lys (SEQ ID No: 13) (see Example 6 above); Ala-Lys-Pro-Ser-Tyr-Hyp-Thr-DOPA-Hyp-Lys (SEQ ID No: 14) (see Example 3 above); and Ala-Lys-Pro-Ser-Tyr-Hyp-Thr-Tyr-Hyp-Lys (SEQ ID No: 15) (see Example 1 above), were made as follows using the following excipients, all of which were sourced from Sinopharm Chemical Reagent Co. Ltd, Shanghai, China, unless otherwise specified.

Stearic acid (2 g), glycerin monostearate (2 g) and hexadecanol (2 g) were mixed together and stirred. The mixture was heated to 85° C. until the mixture had completely melted.

Ammonium acryloyldimethyltaurate/VP copolymer (0.13 g; Clariant Chemical Co., Ltd., Guangzhou, China), purified water (87.02 g). and sodium hydroxide (0.25 g) were mixed together at 85° C. and stirred to form a homogeneous colloidal suspension. Then, glycerin (5 g), phenoxyethanol (0.3 g) and ethylhexyl glycerin 0.1 g (latter two reagents both Shanghai Rayson Chemicals Co., Ltd., Shanghai, China) were added to the mixture with constant stirring.

200 mg of each of the four peptides were dissolved in 1 g of purified water.

The copolymer/water mixture and sorbitan stearate-containing mixture were combined as described in Example 7 above. The resultant emulsion was cooled to 55° C. and then the solution containing Ala-Lys-Pro-Ser-Tyr-Hyp-Hyp-Thr-DOPA-Hyp-Lys (SEQ ID No: 12) was mixed in. Cooling to room temperature gave the finished product.

The procedure was repeated for the other three peptides.

Example 9

Lotion Formulations

Body lotions comprising 100 mg each of the peptides Lys-Pro-Ser-Tyr-Hyp-Hyp-Thr-DOPA-Hyp-Lys (SEQ ID No: 4); Lys-Pro-Ser-Tyr-Hyp-Hyp-Thr-Tyr-Hyp-Lys (SEQ ID No: 5); Lys-Pro-Ser-Tyr-Hyp-Thr-DOPA-Hyp-Lys (SEQ ID No: 6); and Lys-Pro-Ser-Tyr-Hyp-Thr-Tyr-Hyp-Lys (SEQ ID No: 7); Ser-Lys-Pro-Ser-Tyr-Hyp-Hyp-Thr-DOPA-Lys (SEQ ID No: 8); Ser-Lys-Pro-Ser-Tyr-Hyp-Hyp-Thr-Tyr-Lys (SEQ ID No: 9); Ser-Lys-Pro-Ser-Tyr-Hyp-Thr-DOPA-Hyp-Lys (SEQ ID No: 10); and Ser-Lys-Pro-Ser-Tyr-Hyp-Thr-Tyr-Hyp-Thr-Tyr-Hyp-Lys (SEQ ID No: 11) (see Example 6 above), were made as follows using the following excipients, all of which were sourced from Sinopharm Chemical Reagent Co. Ltd, Shanghai, China.

Hydroxypropyl methyl cellulose (HPMC; Cosmetic Grade, 0.1 g), hydroxyethyl cellulose (Cosmetic grade, 0.1 g), glucose, phenoxy alcohol (0.5 g) and purified water (93.2 g) were mixed together and heated to 85° C. with constant stirring until a homogeneous colloidal suspension resulted. The mixture was cooled to room temperature.

100 mg of each of the eight peptides were dissolved in 1 g of purified water. The solution containing Lys-Pro-Ser-Tyr-Hyp-Hyp-Thr-DOPA-Hyp-Lys (SEQ ID No: 4) was added to the colloidal suspension and mixed together until the resultant was mixed for uniformly as the finished product.

The procedure was repeated for the other seven peptides. Further, essentially the same procedure as that described above was employed to make cream-based formulations comprising 10 mg each of the peptides Ala-Lys-Pro-Ser-Tyr-Hyp-Hyp-Thr-DOPA-Hyp-Lys (SEQ ID No: 12); Ala-Lys-Pro-Ser-Tyr-Hyp-Hyp-Thr-Tyr-Hyp-Lys (SEQ ID No: 13) (see Example 6 above); Ala-Lys-Pro-Ser-Tyr-Hyp-Thr-DOPA-Hyp-Lys (SEQ ID No: 14) (see Example 3 above); and Ala-Lys-Pro-Ser-Tyr-Hyp-Thr-Tyr-Hyp-Lys (SEQ ID No: 15) (see Example 1 above).

Example 10

Gel Formulations I

Gel-based formulations comprising each of the peptides Lys-Pro-Ser-Tyr-Hyp-Hyp-Thr-DOPA-Hyp-Lys (SEQ ID No: 4); Lys-Pro-Ser-Tyr-Hyp-Hyp-Thr-Tyr-Hyp-Lys (SEQ ID No: 5); Lys-Pro-Ser-Tyr-Hyp-Thr-DOPA-Hyp-Lys (SEQ ID No: 6); and Lys-Pro-Ser-Tyr-Hyp-Thr-Tyr-Hyp-Lys (SEQ ID No: 7) (see Example 6 above), were prepared in essentially the same way as described in Example 9, except that HPMC (1 g), hydroxyethyl cellulose (1 g), glucose (5 g), phenoxy alcohol (0.5 g) and purified water (91.45 g) were mixed together and heated to 85° C. with constant stirring prior to adding a solution of 50 mg of Lys-Pro-Ser-Tyr-Hyp-Hyp-Thr-DOPA-Hyp-Lys (SEQ ID No: 4) in 1 g of purified water.

Complete mixing gave the finished product and the procedure was repeated for the other three peptides.

Example 11

Gel Formulations II

Gel-based formulations comprising each of the peptides Ser-Lys-Pro-Ser-Tyr-Hyp-Hyp-Thr-DOPA-Lys (SEQ ID No: 8); Ser-Lys-Pro-Ser-Tyr-Hyp-Hyp-Thr-Tyr-Lys (SEQ ID No: 9); Ser-Lys-Pro-Ser-Tyr-Hyp-Thr-DOPA-Hyp-Lys (SEQ ID No: 10); and Ser-Lys-Pro-Ser-Tyr-Hyp-Thr-Tyr-Hyp-Lys (SEQ ID No: 11) (see Example 6 above), were prepared using a similar process to that described in Example 10 above, but using the following excipients, all of which were sourced from Sinopharm Chemical Reagent Co. Ltd, Shanghai, China.

Methyl cellulose (Cosmetic grade, 2.2 g), glycerol (11 g), propanediol (11 g) and purified water (74.75 g) were mixed together and stirred for 10 hours to obtain a homogeneous colloidal suspension.

50 mg of Ser-Lys-Pro-Ser-Tyr-Hyp-Hyp-Thr-DOPA-Lys (SEQ ID No: 8), pre-dissolved in 1 g of purified water was the added with mixing to obtain a uniform finished product.

The procedure was repeated for the other three peptides.

Essentially the same procedure was employed to make gel formulations comprising 150 mg each of the peptides Ala-Lys-Pro-Ser-Tyr-Hyp-Hyp-Thr-DOPA-Hyp-Lys (SEQ ID No: 12); Ala-Lys-Pro-Ser-Tyr-Hyp-Hyp-Thr-Tyr-Hyp-Lys (SEQ ID No: 13) (see Example 6 above); Ala-Lys-Pro-Ser-Tyr-Hyp-Thr-DOPA-Hyp-Lys (SEQ ID No: 14) (see Example 3 above); and Ala-Lys-Pro-Ser-Tyr-Hyp-Thr-Tyr-Hyp-Lys (SEQ ID No: 15) (see Example 1 above), except that 1 g of carbomer (Sinopharm Chemical Reagent Co. Ltd) was used in place of methyl cellulose, and 5 g of glycerol was used along with 82.85 g of purified water.

Example 12

Gel Formulations III

Skin care gel-based compositions based on the peptides Lys-Pro-Ser-Tyr-Hyp-Hyp-Thr-DOPA-Hyp-Lys (SEQ ID No: 4); Lys-Pro-Ser-Tyr-Hyp-Hyp-Thr-Tyr-Hyp-Lys (SEQ ID No: 5); Lys-Pro-Ser-Tyr-Hyp-Thr-DOPA-Hyp-Lys (SEQ ID No: 6); and Lys-Pro-Ser-Tyr-Hyp-Thr-Tyr-Hyp-Lys (SEQ ID No: 7) (see Example 6 above) were made.

First sodium hyaluronate (0.2 g; Sinopharm Chemical Reagent Co. Ltd was swelled in purified water (98.75 g) for 24 hours 50 mg of Lys-Pro-Ser-Tyr-Hyp-Hyp-Thr-DOPA-Hyp-Lys (SEQ ID No: 4) pre-dissolved in 1 g of purified water was added to the sodium hyaluronate gel and mixed well to obtain the finished product. The procedure was repeated for the other three peptides.

Essentially the same procedure was employed to make gel formulations comprising 20 mg each of the peptides Ser-Lys-Pro-Ser-Tyr-Hyp-Hyp-Thr-DOPA-Lys (SEQ ID No: 8); Ser-Lys-Pro-Ser-Tyr-Hyp-Hyp-Thr-Tyr-Lys (SEQ ID No: 9); Ser-Lys-Pro-Ser-Tyr-Hyp-Thr-DOPA-Hyp-Lys (SEQ ID No: 10); and Ser-Lys-Pro-Ser-Tyr-Hyp-Thr-Tyr-Hyp-Lys (SEQ ID No: 11) (see Example 6 above), except that, this time, 0.1 g of sodium hyaluronate was added to 94.88 g of purified water prior to adding, in each case, separately pre-prepared solutions, each comprising 20 mg of each peptide in 1 g of purified water, along with butanediol (2 g) and pentanediol (2 g) (both Sinopharm Chemical Reagent Co. Ltd), with mixing, to obtain the finished products.

Similarly, gel formulations were made from Ala-Lys-Pro-Ser-Tyr-Hyp-Hyp-Thr-DOPA-Hyp-Lys (SEQ ID No: 12); Ala-Lys-Pro-Ser-Tyr-Hyp-Hyp-Thr-Tyr-Hyp-Lys (SEQ ID No: 13) (see Example 6 above); Ala-Lys-Pro-Ser-Tyr-Hyp-Thr-DOPA-Hyp-Lys (SEQ ID No: 14) (see Example 3 above); and Ala-Lys-Pro-Ser-Tyr-Hyp-Thr-Tyr-Hyp-Lys (SEQ ID No: 15) (see Example 1 above), as well as Lys-Pro-Ser-Tyr-Hyp-Hyp-Thr-DOPA-Hyp (SEQ ID No: 16); Lys-Pro-Ser-Tyr-Hyp-Hyp-Thr-Tyr-Hyp (SEQ ID No: 17); Lys-Pro-Ser-Tyr-Hyp-Thr-DOPA-Hyp (SEQ ID No: 18); and Lys-Pro-Ser-Tyr-Hyp-Thr-Tyr-Hyp (SEQ ID No: 19) (see Example 6 above), in each case using 0.4 g of sodium hyaluronate in 96.4 g (first four peptides) or 96.5 g (last four peptides) of purified water, and adding 2 g of butanediol (only) along with separately pre-prepared solutions comprising 200 mg of each of the first four peptides, and 100 mg of each the last four peptides, each of which were dissolved in 1 g of purified water, to make eight separate gel products.

Example 13

Skin Tonics

Skin tonics were made by dissolving the following amounts of each of the following peptides in the specified amount of purified water:

(a)
```
                                    (SEQ ID No: 4)
Lys-Pro-Ser-Tyr-Hyp-Hyp-Thr-DOPA-Hyp-Lys;

(SEQ ID No: 5)
Lys-Pro-Ser-Tyr-Hyp-Hyp-Thr-Tyr-Hyp-Lys;

(SEQ ID No: 6)
Lys-Pro-Ser-Tyr-Hyp-Thr-DOPA-Hyp-Lys;
and (SEQ ID No: 7)
Lys-Pro-Ser-Tyr-Hyp-Thr-Tyr-Hyp-Lys (see
Example 6 above), 20 mg of each peptide in
99.98 g.
```

36

-continued
```
(b)
                                    (SEQ ID No: 8)
Ser-Lys-Pro-Ser-Tyr-Hyp-Hyp-Thr-DOPA-Lys;

(SEQ ID No: 9)
Ser-Lys-Pro-Ser-Tyr-Hyp-Hyp-Thr-Tyr-Lys;

(SEQ ID No: 10)
Ser-Lys-Pro-Ser-Tyr-Hyp-Thr-DOPA-Hyp-Lys;
and (SEQ ID No: 11)
Ser-Lys-Pro-Ser-Tyr-Hyp-Thr-Tyr-Hyp-Lys (see
Example 6 above), 100 mg of each peptide in
99.9 g.

(c)
                                    (SEQ ID No: 12)
Ala-Lys-Pro-Ser-Tyr-Hyp-Hyp-Thr-DOPA-Hyp-Lys;
and (SEQ ID No: 13)
Ala-Lys-Pro-Ser-Tyr-Hyp-Hyp-Thr-Tyr-Hyp-Lys
(see Example 6 above),, 10 mg of each peptide
in 99.99 g (d)
                                    (SEQ ID No: 14)
Ala-Lys-Pro-Ser-Tyr-Hyp-Thr-DOPA-Hyp-Lys (see
Example 3 above), 10 mg in 99.99 g.

(e)
                                    (SEQ ID No: 15)
Ala-Lys-Pro-Ser-Tyr-Hyp-Thr-Tyr-Hyp-Lys (see
Example 1 above), 10 mg in 99.99 g.

(f)
                                    (SEQ ID No: 16)
Lys-Pro-Ser-Tyr-Hyp-Hyp-Thr-DOPA-Hyp;

(SEQ ID No: 17)
Lys-Pro-Ser-Tyr-Hyp-Hyp-Thr-Tyr-Hyp;

(SEQ ID No: 18)
Lys-Pro-Ser-Tyr-Hyp-Thr-DOPA-Hyp;
and (SEQ ID No: 19)
Lys-Pro-Ser-Tyr-Hyp-Thr-Tyr-Hyp (see Example
6 above), 100 mg of each peptide in 99.9 g.

(g)
                                    (SEQ ID No: 20)
Ser-Lys-Pro-Ser-Tyr-Hyp-Hyp-Thr-DOPA;

(SEQ ID No: 21)
Ser-Lys-Pro-Ser-Tyr-Hyp-Hyp-Thr-Tyr;

(SEQ ID No: 22)
Ser-Lys-Pro-Ser-Tyr-Hyp-Thr-DOPA-Hyp;
and (SEQ ID No: 23)
Ser-Lys-Pro-Ser-Tyr-Hyp-Thr-Tyr-Hyp (see
Example 6 above), 40 mg of each peptide in
99.96 g.

(h)
                                    (SEQ ID No: 24)
Ala-Lys-Pro-Ser-Tyr-Hyp-Hyp-Thr-DOPA-Hyp;

(SEQ ID No: 25)
Ala-Lys-Pro-Ser-Tyr-Hyp-Hyp-Thr-Tyr-Hyp;
```

37
-continued (SEQ ID No: 26)
Ala-Lys-Pro-Ser-Tyr-Hyp-Thr-DOPA-Hyp;
and (SEQ ID No: 27)
Ala-Lys-Pro-Ser-Tyr-Hyp-Thr-Tyr-Hyp (see
Example 6 above), 60 mg of each peptide in
99.94 g.

In each case, appropriate preservatives and/or moisturizers may be added to the skin tonics to provide a better skin feeling.

Example 14

Moisturizing Sprays

Moisturizing sprays based on the peptides Lys-Pro-Ser-Tyr-Hyp-Hyp-Thr-DOPA-Hyp (SEQ ID No: 16); Lys-Pro-Ser-Tyr-Hyp-Hyp-Thr-Tyr-Hyp (SEQ ID No: 17); Lys-Pro-Ser-Tyr-Hyp-Thr-DOPA-Hyp (SEQ ID No: 18); and Lys-Pro-Ser-Tyr-Hyp-Thr-Tyr-Hyp (SEQ ID No: 19) (see Example 6 above), were made in the following way using the following excipients, all of which were sourced from Sinopharm Chemical Reagent Co. Ltd, Shanghai, China.

First 10 mg of each peptide were dissolved in 1 g of purified water to obtain four peptide skin tonics. Then, EDTA disodium (0.02 g), butanediol (1.5 g), arginine (0.02 g), hexanediol (0.5 g) and purified water (96.95 g) were mixed together.

The peptide solution comprising Lys-Pro-Ser-Tyr-Hyp-Hyp-Thr-DOPA-Hyp (SEQ ID No: 16) was added to the resultant solution to obtain the finished product. The procedure was repeated for the other three peptides.

Example 15

Essences

Essences based on the peptides Ser-Lys-Pro-Ser-Tyr-Hyp-Hyp-Thr-DOPA (SEQ ID No: 20); Ser-Lys-Pro-Ser-Tyr-Hyp-Hyp-Thr-Tyr (SEQ ID No: 21); Ser-Lys-Pro-Ser-Tyr-Hyp-Thr-DOPA-Hyp (SEQ ID No: 22); and Ser-Lys-Pro-Ser-Tyr-Hyp-Thr-Tyr-Hyp (SEQ ID No: 23) (see Example 6 above), were made in the following way using the following excipients, all of which were sourced from Sinopharm Chemical Reagent Co. Ltd, Shanghai, China.

Sodium hyaluronate (0.5 g) and carbomer (0.04 g) were added to 98.36 g of purified water. After 24 hours, a swollen gel resulted.

Each of the four peptides (100 mg) were dissolved in 1 g of purified water. The resultant solution comprising Ser-Lys-Pro-Ser-Tyr-Hyp-Hyp-Thr-DOPA (SEQ ID No: 20) was added to the sodium hyaluronate/carbomer mixture. Thorough mixing gave the finished product.

The procedure was repeated for the other three peptides.

Example 16

Synthetic Peptides As a Peptide Glue

Ala-Lys-Pro-Ser-Tyr-Hyp-Thr-DOPA-Hyp-Lys (SEQ ID No: 14) (see Example 3 above) was firstly dissolved in pure water (as well as aqueous solutions comprising an acetate buffer, and a phosphate buffers) at pHs between 2 and 8.

Various peptide mixtures were prepared with concentrations between 100 and 800 mg/g. After the peptide was fully dissolved, the clear solution was used as an adhesive.

SEQUENCE LISTING

The instant application contains a Sequence Listing which has been submitted electronically in ASCII format and is hereby incorporated by reference in its entirety. Said ASCII copy, created on Nov. 24, 2025, is named 147432_001440_Revised.txt and is 16,500 bytes in size.

The invention claimed is:

1. A compound which consists of the amino acid sequence:

```
                              (SEQ ID NO: 15)
    Ala-Lys-Pro-Ser-Tyr-Hyp-Thr-Tyr-Hyp-Lys.
```

2. A formulation comprising a compound as defined in claim 1 and a pharmaceutically- or a cosmetically-acceptable, adjuvant, diluent or carrier.

3. The formulation as claimed in claim 2 that is suitable for, adapted for, and/or packaged and presented for, topical administration, wherein the pharmaceutically- or cosmetically-acceptable adjuvant, diluent or carrier is a topical adjuvant, diluent or carrier.

4. The formulation as claimed in claim 2, which is in the form of a gel, a spray, a cream, an ointment or a dry powder.

5. The formulation as claimed in claim 2, which further includes another antiinflammatory agent.

6. A kit of parts comprising components:
(A) a pharmaceutical formulation as defined in claim 2; and
(B) a pharmaceutical formulation including another anti-inflammatory agent in admixture with a pharmaceutically-acceptable adjuvant, diluent or carrier,
which components (A) and (B) are each provided in a form that is suitable for administration in conjunction with the other.

7. A method of treatment of inflammation, an inflammatory disorder, and/or of a disorder characterised by inflammation, which method comprises the administration of a compound as defined in claim 1 to a patient in need of such treatment.

8. The method as claimed in claim 7, wherein the inflammatory disorder is a disorder of the mucosa selected from the group consisting of allergic rhinitis, conjunctivitis, an ano-rectal disease, an inflammatory bowel disease, a gyneco-logical disease, a gastrointestinal disease, and a dental disease.

9. The method as claimed in claim 8, wherein the ano-rectal disease is selected from the group consisting of diarrhea, hemorrhoids, an anal abscess, a fistula, a fissure, anal itching, anal sinusitis, anal warts, radiation proctitis, and rectal prolapse.

10. The method as claimed in claim 8, wherein the gynecological disease is selected from the group consisting of cervicitis, vaginitis, colpitis, and pelvic pain.

11. The method as claimed in claim 8, wherein the inflammatory bowel disease is ulcerative colitis or Crohn's disease.

12. The method as claimed in claim 8, wherein the dental disease is periodontitis.

13. The method as claimed in claim 8, wherein the gastrointestinal disease is stomatitis, gastroesophageal reflux disease, esophageal burn, a gastric ulcer or a duodenal ulcer.

14. The method as claimed in claim 7, wherein the disorder characterised by inflammation is, or results in, a wound or a burn.

15. The method as claimed in claim 14, wherein the disorder resulting in a wound is hemorrhoids or ulcerative colitis.

16. A method of treatment of fibrosis, a fibrotic disorder, and/or of a disorder characterised by fibrosis, which method comprises the administration of a compound as defined in claim 1, to a patient in need of such treatment.

17. The method as claimed in claim 16, wherein the fibrosis is fibrosis of the vagina or the cervix.

18. The method as claimed in claim 7, wherein adminis-tering the compound is orally, intravenously, cutaneously, subcutaneously, nasally, intramuscularly, intraperitoneally, via the pulmonary, or anorectally.

19. A process for the preparation of a formulation, which process comprises bringing into association a compound as defined in claim 1 with one or more pharmaceutically-acceptable, or cosmetically-acceptable, adjuvant, diluent or carrier.

20. A process for the preparation of a kit of parts as defined in claim 6, which process comprises bringing into association component (A) of the kit of parts with compo-nent (B) of the kit of parts.

21. The method as claimed in claim 7, wherein the compound is administered topically in the form of a topical formulation.

22. The method as claimed in claim 21, wherein the relevant condition is treated by way of direct topical admin-istration to skin or a mucosal surface.

* * * * *

```
SEQUENCE LISTING

<160> NUMBER OF SEQ ID NOS: 41

<210> SEQ ID NO 1
<211> LENGTH: 10
<212> TYPE: PRT
<213> ORGANISM: Mytilus sp.
<220> FEATURE:
<223> OTHER INFORMATION: Mefp-1 decapeptide
<220> FEATURE:
<221> NAME/KEY: SITE
<222> LOCATION: 6,7
<223> OTHER INFORMATION: Wherein Xaa is 3-hydroxyproline or
      4-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 1

Ala Lys Pro Ser Tyr Xaa Xaa Thr Xaa Lys
1               5                   10

<210> SEQ ID NO 2
<211> LENGTH: 10
<212> TYPE: PRT
```

-continued

```
<213> ORGANISM: Artificial Sequence
<220> FEATURE:
<223> OTHER INFORMATION: Synthesized Mefp-1 decapeptide analogue
<220> FEATURE:
<221> NAME/KEY: SITE
<222> LOCATION: 6,7
<223> OTHER INFORMATION: Wherein Xaa is 3-hydroxyproline or
      4-hydroxyproline

<400> SEQUENCE: 2

Ala Lys Pro Ser Tyr Xaa Xaa Thr Tyr Lys
1               5                   10

<210> SEQ ID NO 3
<211> LENGTH: 13
<212> TYPE: PRT
<213> ORGANISM: Artificial Sequence
<220> FEATURE:
<221> NAME/KEY: SITE
<222> LOCATION: 1
<223> OTHER INFORMATION: Wherein Xaa is optionally N-terminally modified
      with a 3,4-dihydrocinnamic acid group, or is not so modified
<220> FEATURE:
<223> OTHER INFORMATION: Synthesized peptide compound
<220> FEATURE:
<221> NAME/KEY: VARIANT
<222> LOCATION: 1
<223> OTHER INFORMATION: Wherein Xaa is absent or is alanine or serine
<220> FEATURE:
<221> NAME/KEY: VARIANT
<222> LOCATION: 3
<223> OTHER INFORMATION: Wherein Xaa is proline, 3-hydroxyproline,
      4-hydroxyproline, 5-hydroxyproline, 3,4-dihydroxyproline,
      3,5-dihydroxyproline, or 4,5-dihydroxyproline
<220> FEATURE:
<221> NAME/KEY: VARIANT
<222> LOCATION: 5
<223> OTHER INFORMATION: Wherein Xaa is absent or is tyrosine or
      3,4-dihydroxyphenylalanine
<220> FEATURE:
<221> NAME/KEY: VARIANT
<222> LOCATION: 6
<223> OTHER INFORMATION: Wherein Xaa is proline, 3-hydroxyproline,
      4-hydroxyproline, 5-hydroxyproline, 3,4-dihydroxyproline,
      3,5-dihydroxyproline, or 4,5-dihydroxyproline
<220> FEATURE:
<221> NAME/KEY: VARIANT
<222> LOCATION: 7
<223> OTHER INFORMATION: Wherein Xaa is selected from the group proline,
      3-, 4-, and 5-hydroxyproline, 3,4-, 3,5-, and
      4,5-dihydroxyproline, threonine, 3,4-dihydroxyphenylalanine, and
      tyrosine
<220> FEATURE:
<221> NAME/KEY: VARIANT
<222> LOCATION: 8..11
<223> OTHER INFORMATION: Wherein Xaa is selected from the group proline,
      3-, 4-, and 5-hydroxyproline, 3,4-, 3,5-, and
      4,5-dihydroxyproline, threonine, 3,4-dihydroxyphenylalanine, and
      tyrosine, or is absent
<220> FEATURE:
<221> NAME/KEY: VARIANT
<222> LOCATION: 12
<223> OTHER INFORMATION: Wherein Xaa is proline, 3-hydroxyproline,
      4-hydroxyproline, 5-hydroxyproline, 3,4-dihydroxyproline,
      3,5-dihydroxyproline, 4,5-dihydroxyproline, threonine,
      3,4-dihydroxyphenylalanine, or tyrosine
<220> FEATURE:
<221> NAME/KEY: VARIANT
<222> LOCATION: 13
<223> OTHER INFORMATION: Wherein Xaa is absent or is lysine

<400> SEQUENCE: 3

Xaa Lys Xaa Ser Xaa Xaa Xaa Xaa Xaa Xaa Xaa Xaa Xaa
1               5                   10
```

```
<210> SEQ ID NO 4
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 5,6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 4

Lys Pro Ser Tyr Xaa Xaa Thr Xaa Xaa Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 5,6,9
<223> OTHER INFORMATION: Wherein Xaa is 3-hydroxyproline,
      4-hydroxyproline, or 5-hydroxyproline

<400> SEQUENCE: 5

Lys Pro Ser Tyr Xaa Xaa Thr Tyr Xaa Lys
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 5,8
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 7
<223> OTHER INFORMATION: Wherein Xaa is 3,4-dihydroxyphenylalanine

<400> SEQUENCE: 6

Lys Pro Ser Tyr Xaa Thr Xaa Xaa Lys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 5,8
<223> OTHER INFORMATION: Wherein Xaa is 3-hydroxyproline,
      4-hydroxyproline, or 5-hydroxyproline

<400> SEQUENCE: 7

Lys Pro Ser Tyr Xaa Thr Tyr Xaa Lys
1               5
```

```
<210> SEQ ID NO 8
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 8

Ser Lys Pro Ser Tyr Xaa Xaa Thr Xaa Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline

<400> SEQUENCE: 9

Ser Lys Pro Ser Tyr Xaa Xaa Thr Tyr Lys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 10

Ser Lys Pro Ser Tyr Xaa Thr Xaa Xaa Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline

<400> SEQUENCE: 11

Ser Lys Pro Ser Tyr Xaa Thr Tyr Xaa Lys
1               5                   10
```

```
<210> SEQ ID NO 12
<211> LENGTH: 11
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,7,10
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 12

Ala Lys Pro Ser Tyr Xaa Xaa Thr Xaa Xaa Lys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,7,10
<223> OTHER INFORMATION: Wherein Xaa is 3-hydroxyproline,
      4-hydroxyproline, or 5-hydroxyproline

<400> SEQUENCE: 13

Ala Lys Pro Ser Tyr Xaa Xaa Thr Tyr Xaa Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 14

Ala Lys Pro Ser Tyr Xaa Thr Xaa Xaa Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline

<400> SEQUENCE: 15

Ala Lys Pro Ser Tyr Xaa Thr Tyr Xaa Lys
```

-continued

```
1               5                  10
```

```
<210> SEQ ID NO 16
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 5,6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 16

Lys Pro Ser Tyr Xaa Xaa Thr Xaa Xaa
1               5
```

```
<210> SEQ ID NO 17
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 5,6,9
<223> OTHER INFORMATION: Wherein Xaa is 3-hydroxyproline,
      4-hydroxyproline, or 5-hydroxyproline

<400> SEQUENCE: 17

Lys Pro Ser Tyr Xaa Xaa Thr Tyr Xaa
1               5
```

```
<210> SEQ ID NO 18
<211> LENGTH: 8
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 5,8
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 7
<223> OTHER INFORMATION: Wherein Xaa is 3,4-dihydroxyphenylalanine

<400> SEQUENCE: 18

Lys Pro Ser Tyr Xaa Thr Xaa Xaa
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 5,8
<223> OTHER INFORMATION: Wherein Xaa is 3-hydroxyproline,
      4-hydroxyproline, or 5-hydroxyproline

<400> SEQUENCE: 19
```

-continued

```
Lys Pro Ser Tyr Xaa Thr Tyr Xaa
1               5

<210> SEQ ID NO 20
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 20

Ser Lys Pro Ser Tyr Xaa Xaa Thr Xaa
1               5

<210> SEQ ID NO 21
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline

<400> SEQUENCE: 21

Ser Lys Pro Ser Tyr Xaa Xaa Thr Tyr
1               5

<210> SEQ ID NO 22
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 22

Ser Lys Pro Ser Tyr Xaa Thr Xaa Xaa
1               5

<210> SEQ ID NO 23
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline

<400> SEQUENCE: 23
```

-continued

```
Ser Lys Pro Ser Tyr Xaa Thr Tyr Xaa
1               5

<210> SEQ ID NO 24
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,7,10
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 24

Ala Lys Pro Ser Tyr Xaa Xaa Thr Xaa Xaa
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,7,10
<223> OTHER INFORMATION: Wherein Xaa is 3-hydroxyproline,
      4-hydroxyproline, or 5-hydroxyproline

<400> SEQUENCE: 25

Ala Lys Pro Ser Tyr Xaa Xaa Thr Tyr Xaa
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 26

Ala Lys Pro Ser Tyr Xaa Thr Xaa Xaa
1               5

<210> SEQ ID NO 27
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline
```

```
<400> SEQUENCE: 27

Ala Lys Pro Ser Tyr Xaa Thr Tyr Xaa
1               5

<210> SEQ ID NO 28
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid group
<220> FEATURE:
<223> OTHER INFORMATION: Synthesized peptide compound
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline

<400> SEQUENCE: 28

Ala Lys Pro Ser Tyr Xaa Xaa Thr Tyr Lys
1               5                   10

<210> SEQ ID NO 29
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid group
<220> FEATURE:
<223> OTHER INFORMATION: Synthesized peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline

<400> SEQUENCE: 29

Ala Lys Pro Ser Tyr Xaa Thr Tyr Xaa Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 5,8
<223> OTHER INFORMATION: Wherein Xaa is 3,4-dihydroxyphenylalanine
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline

<400> SEQUENCE: 30

Ala Lys Pro Ser Xaa Xaa Thr Xaa Xaa Lys
1               5                   10

<210> SEQ ID NO 31
<211> LENGTH: 9
<212> TYPE: PRT
<213> ORGANISM: Artificial Sequence
<220> FEATURE:
```

```
<223> OTHER INFORMATION: Synthesized peptide compound

<400> SEQUENCE: 31

Ala Lys Pro Ser Pro Thr Tyr Pro Lys
1               5

<210> SEQ ID NO 32
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 3,6,9
<223> OTHER INFORMATION: Wherein Xaa is 3-hydroxyproline,
      4-hydroxyproline, or 5-hydroxyproline

<400> SEQUENCE: 32

Ala Lys Xaa Ser Tyr Xaa Thr Tyr Xaa Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 3,6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 5,8
<223> OTHER INFORMATION: Wherein Xaa is 3,4-dihydroxyphenylalanine

<400> SEQUENCE: 33

Ala Lys Xaa Ser Xaa Xaa Thr Xaa Xaa Lys
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 3,6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 34

Ala Lys Xaa Ser Tyr Xaa Thr Xaa Xaa Lys
1               5                   10

<210> SEQ ID NO 35
<211> LENGTH: 9
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid group
```

-continued

```
<220> FEATURE:
<223> OTHER INFORMATION: Synthesized peptide compound
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline

<400> SEQUENCE: 35

Ala Lys Pro Ser Tyr Xaa Xaa Thr Tyr
1               5

<210> SEQ ID NO 36
<211> LENGTH: 9
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid group
<220> FEATURE:
<223> OTHER INFORMATION: Synthesized peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline

<400> SEQUENCE: 36

Ala Lys Pro Ser Tyr Xaa Thr Tyr Xaa
1               5

<210> SEQ ID NO 37
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 5,8
<223> OTHER INFORMATION: Wherein Xaa is 3,4-dihydroxyphenylalanine
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline

<400> SEQUENCE: 37

Ala Lys Pro Ser Xaa Xaa Thr Xaa Xaa
1               5

<210> SEQ ID NO 38
<211> LENGTH: 8
<212> TYPE: PRT
<213> ORGANISM: Artificial Sequence
<220> FEATURE:
<223> OTHER INFORMATION: Synthesized peptide compound

<400> SEQUENCE: 38

Ala Lys Pro Ser Pro Thr Tyr Pro
1               5

<210> SEQ ID NO 39
<211> LENGTH: 9
<212> TYPE: PRT
<213> ORGANISM: Artificial Sequence
<220> FEATURE:
<223> OTHER INFORMATION: Synthesized peptide compound
<220> FEATURE:
```

```
<221> NAME/KEY: SITE
<222> LOCATION: 3,6,9
<223> OTHER INFORMATION: Wherein Xaa is 3-hydroxyproline,
      4-hydroxyproline, or 5-hydroxyproline

<400> SEQUENCE: 39

Ala Lys Xaa Ser Tyr Xaa Thr Tyr Xaa
1               5

<210> SEQ ID NO 40
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 3,6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 5,8
<223> OTHER INFORMATION: Wherein Xaa is 3,4-dihydroxyphenylalanine

<400> SEQUENCE: 40

Ala Lys Xaa Ser Xaa Xaa Thr Xaa Xaa
1               5

<210> SEQ ID NO 41
<211> LENGTH: 9
<212> TYPE: PRT
<213> ORGANISM: Artificial Sequence
<220> FEATURE:
<223> OTHER INFORMATION: Synthesized peptide compound
<220> FEATURE:
<221> NAME/KEY: SITE
<222> LOCATION: 3,6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 41

Ala Lys Xaa Ser Tyr Xaa Thr Xaa Xaa
1               5
```